(12) United States Patent
Eidenschink

(10) Patent No.: US 6,517,515 B1
(45) Date of Patent: Feb. 11, 2003

(54) CATHETER HAVING VARIABLE SIZE GUIDE WIRE LUMEN

(75) Inventor: Tracee E. J. Eidenschink, Wayzata, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/233,553

(22) Filed: Jan. 20, 1999

Related U.S. Application Data

(63) Continuation-in-part of application No. 09/034,421, filed on Mar. 4, 1998, now Pat. No. 6,113,579.

(51) Int. Cl.$^7$ .......................................... A61M 29/00
(52) U.S. Cl. ............................ 604/101.05; 604/99.04
(58) Field of Search ..................... 604/101.01, 101.03, 604/101.04, 101.05, 102.01, 102.03, 96.01, 99.01, 99.02, 99.04; 606/108, 194

(56) References Cited

U.S. PATENT DOCUMENTS

| | | | |
|---|---|---|---|
| 3,631,848 A | 1/1972 | Muller | 128/2.05 R |
| 3,766,915 A | 10/1973 | Rychlik | 128/214.4 |
| 3,788,326 A | 1/1974 | Jacobs | 128/305 |
| 3,911,927 A | 10/1975 | Rich et al. | 128/349 R |
| 3,915,171 A | * 10/1975 | Shermeta | 128/348 |
| 4,085,185 A | 4/1978 | Adair | 264/248 |
| 4,195,637 A | 4/1980 | Grüntzig et al. | 128/348 |
| 4,249,536 A | 2/1981 | Vega | 128/349 B |
| 4,251,305 A | 2/1981 | Becker et al. | 156/86 |
| 4,307,722 A | 12/1981 | Evans | 128/344 |
| 4,323,071 A | 4/1982 | Simpson et al. | 128/343 |
| 4,385,635 A | 5/1983 | Ruiz | 128/658 |
| 4,413,989 A | 11/1983 | Schjeldahl et al. | 604/96 |
| 4,425,919 A | 1/1984 | Alston, Jr. et al. | 128/348 |
| 4,530,698 A | 7/1985 | Goldstein et al. | 604/271 |
| 4,531,512 A | 7/1985 | Wolvek et al. | 128/1 D |
| 4,531,943 A | 7/1985 | Van Tassel et al. | 604/280 |
| 4,540,404 A | 9/1985 | Wolvek | 604/96 |
| 4,551,292 A | 11/1985 | Fletcher et al. | 264/139 |

(List continued on next page.)

FOREIGN PATENT DOCUMENTS

| | | |
|---|---|---|
| AU | A-64747/94 | 3/1995 |
| EP | 0 171 884 A1 | 2/1986 |
| EP | 0 237 564 B1 | 9/1987 |

(List continued on next page.)

OTHER PUBLICATIONS

Melvin I. Kohan, *Nylon Plastics Handbook*, Hanser/Gardner Publications, Inc., Cincinnati, Ohio, Copyright 1995, pp. 378–387.

*Plastics Digest*, vol. 2, Ed. 15, 1994, p. 2–314.

*Primary Examiner*—Sharon Kennedy
(74) *Attorney, Agent, or Firm*—Crompton, Seager & Tufte, LLC

(57) ABSTRACT

A balloon catheter having a first balloon member and a second distal expandable member. The increased distal profile of the catheter with inflation of the second distal expandable member can deflect the distal-most end away from stent walls and edges. Another catheter has a distal region including longitudinal slits and a pre-stressed body configured to expand upon exposure to warm body fluids. Another catheter has a distal region including a first, inner tube disposed about a second, innermost tube. The inner and innermost tubes are secured at the distal-most end. The distal region includes longitudinal slits through the inner tube, thereby defining flaps between the slits. The innermost tube can be retracted relative to the inner tube disposed about the innermost tube, thereby causing the longitudinal flaps to expand outward, thereby increasing the maximum radial extent of the distal region. In yet another embodiment, a balloon catheter having a first guide wire tube is provided. A second guide wire tube is also provided, adapted to be received within the larger, first guide wire tube.

9 Claims, 9 Drawing Sheets

U.S. PATENT DOCUMENTS

| | | | |
|---|---|---|---|
| 4,581,019 A | 4/1986 | Curelaru et al. | 604/164 |
| 4,582,181 A | 4/1986 | Samson | 128/348.1 |
| 4,588,399 A | 5/1986 | Nebergall et al. | 604/280 |
| 4,596,563 A | 6/1986 | Pande | 604/264 |
| 4,610,662 A * | 9/1986 | Weikl et al. | 604/53 |
| 4,616,653 A | 10/1986 | Samson et al. | 128/344 |
| 4,636,272 A | 1/1987 | Riggs | 156/158 |
| 4,636,346 A | 1/1987 | Gold et al. | 264/139 |
| 4,676,229 A | 6/1987 | Krasnicki et al. | 128/4 |
| 4,699,611 A | 10/1987 | Bowden | 604/51 |
| 4,706,670 A | 11/1987 | Andersen et al. | 128/344 |
| 4,739,768 A | 4/1988 | Engelson | 128/658 |
| 4,748,982 A | 6/1988 | Horzewski et al. | 128/344 |
| 4,753,765 A | 6/1988 | Pande | 264/149 |
| 4,759,748 A | 7/1988 | Reed | 604/95 |
| 4,764,324 A | 8/1988 | Burnham | 264/103 |
| 4,777,951 A | 10/1988 | Cribier et al. | 128/344 |
| 4,782,834 A | 11/1988 | Maguire et al. | 128/344 |
| 4,790,331 A | 12/1988 | Okada et al. | 128/772 |
| 4,798,586 A | 1/1989 | Stevens | 604/96 |
| 4,808,164 A | 2/1989 | Hess | 604/95 |
| 4,817,613 A | 4/1989 | Jaraczewski et al. | 128/658 |
| 4,819,751 A | 4/1989 | Shimada et al. | 128/344 |
| 4,820,349 A | 4/1989 | Saab | 128/344 |
| 4,846,174 A | 7/1989 | Willard et al. | 128/344 |
| 4,848,344 A | 7/1989 | Sos et al. | 128/344 |
| 4,863,442 A | 9/1989 | DeMello et al. | 604/282 |
| 4,884,573 A | 12/1989 | Wijay et al. | 128/344 |
| 4,886,506 A | 12/1989 | Lovgren et al. | 604/280 |
| RE33,166 E | 2/1990 | Samson | 606/194 |
| 4,898,896 A | 2/1990 | Maj et al. | 528/323 |
| 4,906,244 A | 3/1990 | Pinchuk et al. | 606/194 |
| 4,917,666 A | 4/1990 | Solar et al. | 604/95 |
| 4,323,071 A | 5/1990 | Simpson et al. | 128/343 |
| 4,921,483 A | 5/1990 | Wijay et al. | 604/96 |
| 4,943,278 A | 7/1990 | Euteneuer et al. | 604/96 |
| 4,946,466 A | 8/1990 | Pinchuk et al. | 606/194 |
| 4,950,227 A | 8/1990 | Savin et al. | 604/8 |
| 4,955,377 A | 9/1990 | Lennox et al. | 128/401 |
| 4,960,410 A | 10/1990 | Pinchuk | 604/96 |
| 4,964,409 A | 10/1990 | Tremulis | 128/657 |
| 4,964,853 A | 10/1990 | Sugiyama et al. | 604/96 |
| 4,976,720 A | 12/1990 | Machold et al. | 606/194 |
| 4,983,168 A | 1/1991 | Moorehead | 604/161 |
| 4,990,139 A * | 2/1991 | Jang | 604/101 |
| 4,994,018 A | 2/1991 | Saper | 600/18 |
| 5,002,559 A | 3/1991 | Tower | 606/194 |
| 5,007,434 A | 4/1991 | Doyle et al. | 128/772 |
| 5,047,045 A | 9/1991 | Arney et al. | 606/194 |
| 5,050,606 A | 9/1991 | Tremulis | 128/637 |
| 5,054,501 A | 10/1991 | Chuttani et al. | 128/772 |
| 5,055,101 A | 10/1991 | McCoy | 604/95 |
| 5,078,702 A | 1/1992 | Pomeranz | 604/280 |
| 5,078,727 A | 1/1992 | Hannam et al. | 606/194 |
| 5,093,546 A | 3/1992 | Matsumiya et al. | 219/10.41 |
| 5,100,381 A | 3/1992 | Burns | 604/96 |
| 5,104,377 A * | 4/1992 | Levine | 604/101 |
| 5,108,416 A | 4/1992 | Ryan et al. | 606/194 |
| 5,120,308 A | 6/1992 | Hess | 604/95 |
| 5,122,125 A | 6/1992 | Deuss | 604/282 |
| 5,139,496 A | 8/1992 | Hed | 606/23 |
| 5,143,093 A | 9/1992 | Sahota | 128/898 |
| 5,147,377 A | 9/1992 | Sahota | 606/194 |
| 5,154,725 A | 10/1992 | Leopold | 606/194 |
| 5,156,594 A | 10/1992 | Keith | 604/96 |
| 5,156,612 A | 10/1992 | Pinchuk et al. | 606/194 |
| 5,158,548 A | 10/1992 | Lau et al. | 604/96 |
| 5,159,937 A | 11/1992 | Tremulis | 128/772 |
| 5,163,906 A | 11/1992 | Ahmadi | 604/101 |
| 5,171,221 A | 12/1992 | Samson | 604/96 |
| 5,171,230 A | 12/1992 | Eland et al. | 604/250 |
| 5,176,637 A | 1/1993 | Sagae | 604/96 |
| 5,180,585 A | 1/1993 | Jacobson et al. | 424/405 |
| 5,209,728 A | 5/1993 | Kraus et al. | 604/96 |
| 5,213,574 A | 5/1993 | Tucker | 604/93 |
| 5,221,270 A | 6/1993 | Parker | 604/282 |
| 5,226,888 A | 7/1993 | Arney | 604/96 |
| 5,226,889 A | 7/1993 | Sheiban | 604/101 |
| 5,234,416 A | 8/1993 | Macaulay et al. | 604/282 |
| 5,240,537 A | 8/1993 | Bodicky | 156/244.13 |
| 5,254,091 A | 10/1993 | Aliahmad et al. | 604/96 |
| 5,256,144 A | 10/1993 | Kraus et al. | 604/96 |
| 5,258,160 A | 11/1993 | Utsumi et al. | 264/558 |
| 5,259,839 A | 11/1993 | Burns | 604/99 |
| 5,261,878 A | 11/1993 | Galindo | 604/96 |
| 5,270,086 A | 12/1993 | Hamlin | 428/35.2 |
| 5,279,559 A | 1/1994 | Barr | 604/95 |
| 5,279,561 A | 1/1994 | Roucher et al. | 604/96 |
| 5,279,562 A | 1/1994 | Sirhan et al. | 604/96 |
| 5,290,295 A | 3/1994 | Querals et al. | 606/108 |
| 5,304,134 A | 4/1994 | Kraus et al. | 604/96 |
| 5,304,198 A | 4/1994 | Samson | 606/194 |
| 5,316,706 A | 5/1994 | Muni et al. | 264/25 |
| 5,318,032 A | 6/1994 | Lonsbury et al. | 128/658 |
| 5,318,527 A | 6/1994 | Hyde et al. | 604/95 |
| 5,318,529 A | 6/1994 | Kontos | 604/96 |
| 5,318,532 A | 6/1994 | Frassica | 604/96 |
| 5,320,604 A * | 6/1994 | Walker et al. | 604/96 |
| 5,324,257 A | 6/1994 | Osborne et al. | 604/53 |
| 5,324,259 A | 6/1994 | Taylor et al. | 604/96 |
| 5,324,263 A | 6/1994 | Kraus et al. | 604/96 |
| 5,327,885 A | 7/1994 | Griffith | 128/662.06 |
| 5,328,468 A | 7/1994 | Kaneko et al. | 604/96 |
| 5,334,148 A | 8/1994 | Martin | 604/96 |
| 5,334,168 A | 8/1994 | Hemmer | 604/281 |
| 5,335,410 A | 8/1994 | Burnham | 29/452 |
| 5,338,296 A | 8/1994 | Dalessandro et al. | 604/96 |
| 5,342,389 A | 8/1994 | Trotta | 606/194 |
| 5,344,400 A | 9/1994 | Kaneko et al. | 604/96 |
| 5,346,505 A | 9/1994 | Leopold | 606/194 |
| 5,370,615 A | 12/1994 | Johnson | 604/96 |
| 5,370,655 A | 12/1994 | Burns | 606/194 |
| 5,387,193 A | 2/1995 | Miraki | 604/96 |
| 5,389,087 A | 2/1995 | Miraki | 604/247 |
| 5,397,306 A | 3/1995 | Nobuyoshi et al. | 604/96 |
| 5,399,164 A | 3/1995 | Snoke et al. | 604/95 |
| 5,403,292 A | 4/1995 | Ju | 604/282 |
| 5,405,338 A | 4/1995 | Kranys | 604/282 |
| 5,405,380 A | 4/1995 | Gianotti et al. | 623/1 |
| 5,407,432 A | 4/1995 | Solar | 604/164 |
| 5,411,477 A | 5/1995 | Saab | 604/96 |
| 5,415,664 A | 5/1995 | Pinchuk | 606/108 |
| 5,423,754 A | 6/1995 | Cornelius et al. | 604/103 |
| 5,423,771 A | 6/1995 | Imran | 604/281 |
| 5,425,709 A | 6/1995 | Gambale | 604/96 |
| 5,425,712 A | 6/1995 | Goodin | 604/96 |
| 5,445,646 A | 8/1995 | Euteneuer et al. | 606/198 |
| 5,449,373 A | 9/1995 | Pinchasik et al. | 606/198 |
| 5,454,788 A | 10/1995 | Walker et al. | 604/96 |
| 5,454,795 A | 10/1995 | Samson | 604/282 |
| 5,458,573 A | 10/1995 | Summers | 604/101 |
| 5,458,613 A | 10/1995 | Gharibadeh et al. | 606/194 |
| 5,470,322 A | 11/1995 | Horzewski et al. | 604/280 |
| 5,480,383 A | 1/1996 | Bagaoisan et al. | 604/96 |
| 5,496,271 A * | 3/1996 | Burton et al. | 604/54 |
| 5,496,294 A | 3/1996 | Hergenrother et al. | 604/282 |
| 5,503,263 A | 4/1996 | Watanabe | 198/442 |
| 5,509,910 A | 4/1996 | Lunn | 604/282 |
| 5,520,644 A | 5/1996 | Imran | 604/95 |
| 5,531,685 A | 7/1996 | Hemmer et al. | 604/95 |
| 5,531,715 A | 7/1996 | Engelson et al. | 604/265 |

| | | | |
|---|---|---|---|
| 5,538,513 A | 7/1996 | Okajima | 604/282 |
| 5,540,236 A | 7/1996 | Ginn | 128/772 |
| 5,542,924 A | 8/1996 | Snoke et al. | 604/95 |
| 5,542,937 A | 8/1996 | Chee et al. | 604/280 |
| 5,549,552 A | 8/1996 | Peters et al. | 604/96 |
| 5,549,556 A | 8/1996 | Ndondo-Lay et al. | 604/102 |
| 5,554,121 A | 9/1996 | Ainsworth et al. | 604/96 |
| 5,554,139 A | 9/1996 | Okajima | 604/282 |
| 5,569,218 A | 10/1996 | Berg | 604/282 |
| 5,588,965 A * | 12/1996 | Burton et al. | 604/101 |
| 5,591,129 A | 1/1997 | Shoup et al. | 604/96 |
| 5,605,543 A | 2/1997 | Swanson | 604/96 |
| 5,624,449 A | 4/1997 | Pham et al. | 606/108 |
| 5,643,209 A | 7/1997 | Fugoso et al. | 604/96 |
| 5,645,528 A | 7/1997 | Thome | 604/96 |
| 5,647,857 A | 7/1997 | Anderson et al. | 604/264 |
| 5,674,198 A * | 10/1997 | Leone | 604/101 |
| 5,716,373 A | 2/1998 | Wolvek et al. | 606/194 |
| 5,718,686 A * | 2/1998 | Davis | 604/101 |
| 5,725,513 A | 3/1998 | Ju et al. | 604/280 |
| 5,728,063 A | 3/1998 | Priessman et al. | 604/96 |
| 5,776,100 A | 7/1998 | Forman | 604/102 |
| 5,891,110 A | 4/1999 | Larson et al. | |
| 5,971,955 A * | 10/1999 | Nap et al. | 604/101 |
| 6,048,338 A | 4/2000 | Larson et al. | |
| 6,102,891 A * | 8/2000 | Maria Van Erp | 604/96 |
| 6,113,579 A | 9/2000 | Eidenschink et al. | |
| 6,287,320 B1 * | 9/2001 | Slepian | 606/194 |

FOREIGN PATENT DOCUMENTS

| | | |
|---|---|---|
| EP | 0 448 886 A1 | 10/1991 |
| EP | 0 452 595 A1 | 10/1991 |
| EP | 0 452 901 B1 | 10/1991 |
| EP | 0 594 201 A2 | 4/1994 |
| EP | 0 688 576 A1 | 12/1995 |
| WO | WO 93/04726 | 3/1993 |
| WO | WO 93/17750 | 9/1993 |
| WO | WO 94/01160 | 1/1994 |
| WO | WO 96/03092 A1 | 2/1996 |
| WO | WO 96/39219 | 12/1996 |

* cited by examiner

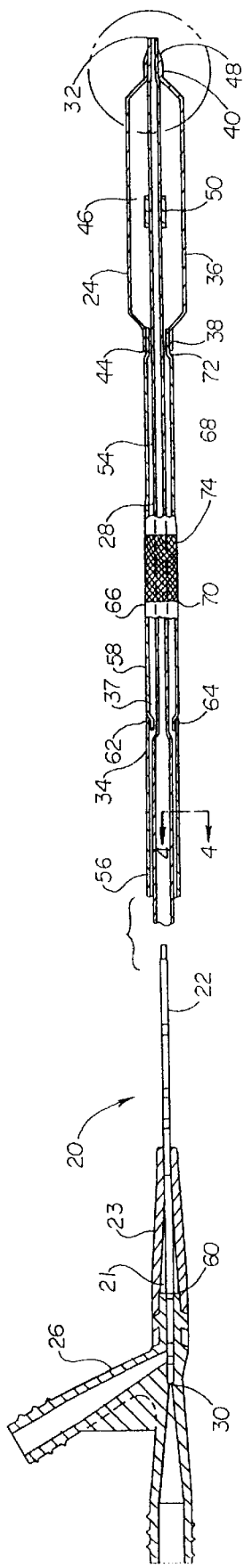
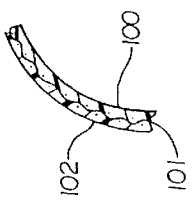
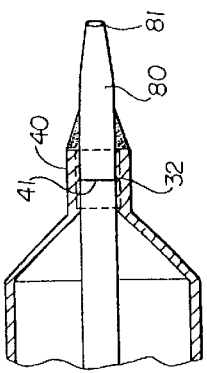
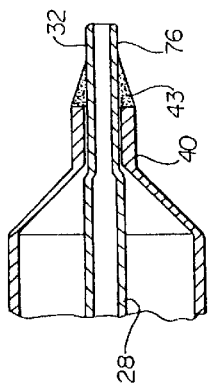

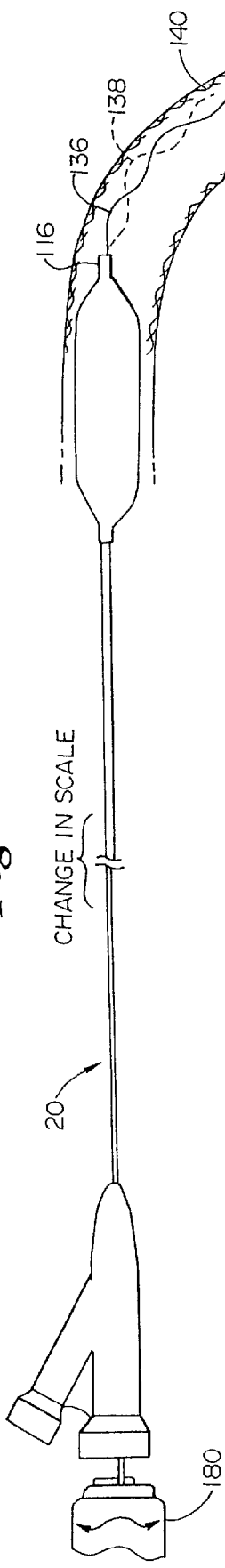
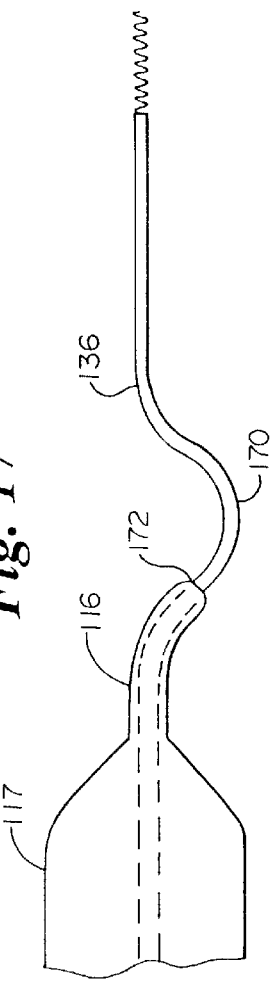
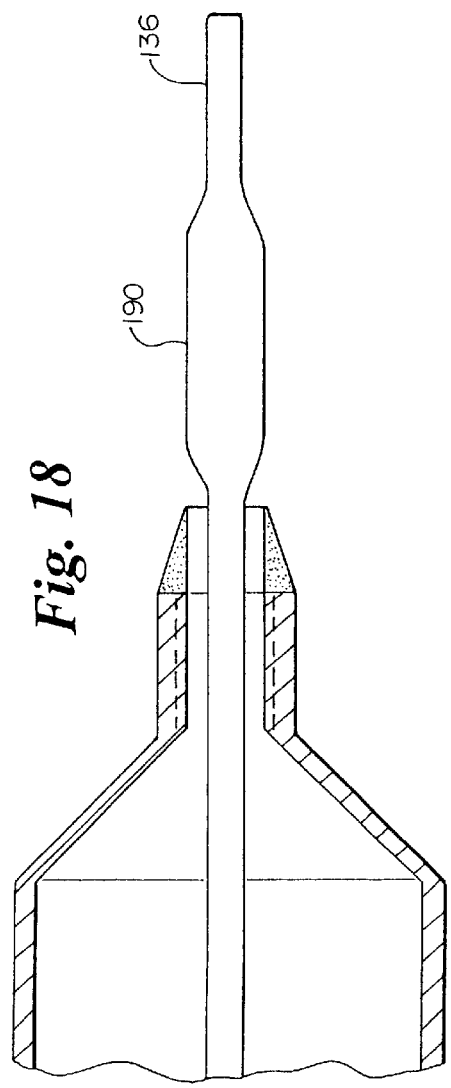
Fig. 16
Fig. 17
Fig. 18

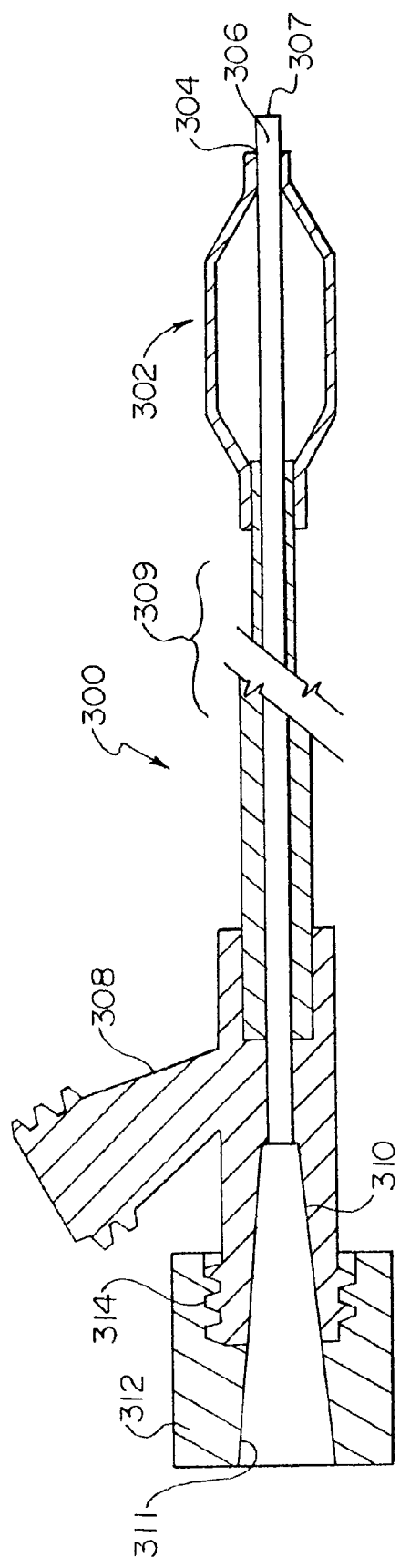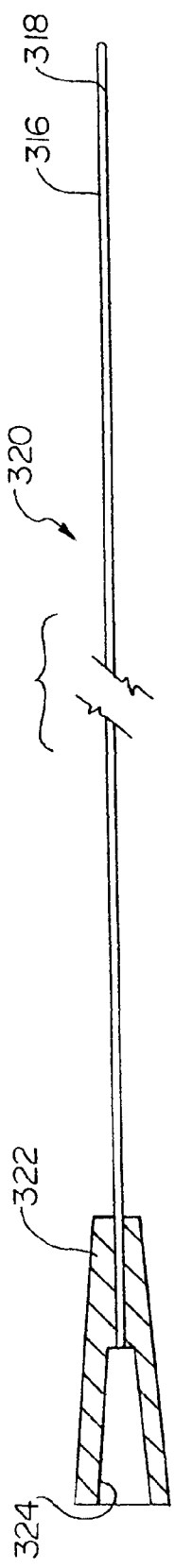

CATHETER HAVING VARIABLE SIZE GUIDE WIRE LUMEN

CROSS REFERENCES TO CO-PENDING APPLICATIONS

The present application is a continuation-in-part of U.S. Patent Ser. No. 09/034,421 filed Mar. 4, 1998 now U.S. Pat. No. 6,113,579, issued Sep. 5, 2000, entitled "CATHETER TIP DESIGNS AND METHODS FOR IMPROVED STENT CROSSING".

FIELD OF THE INVENTION

The present invention is generally related to medical devices. More specifically, the present invention is related to intravascular catheters having improved tips and guide wire lumens. The present invention includes catheters having an inflatable bulbous tip, a tip pre-stressed to expand outward, an expandable tip, and an inner-most guide wire tube disposed within an inner guide wire tube.

BACKGROUND OF THE INVENTION

Intravascular diseases are commonly treated by relatively non-invasive catheter-based techniques such as percutaneous transluminal angioplasty (PTA) and percutaneous transluminal coronary angioplasty (PTCA). Catheter-based treatment and diagnostic techniques can also include atherectomy, laser radiation, ultrasonic imaging along with others. These therapeutic techniques are well known in the art and typically involve the use of a catheter, such as a balloon catheter or catheter having some other therapeutic device located proximate a distal end of the catheter, with a guide wire, possibly in combination with other intravascular devices. A typical balloon catheter has an elongate shaft with a balloon attached proximate the distal end and a manifold attached to the proximal end. In use, a balloon catheter is advanced over a guide wire such that the balloon is positioned adjacent a restriction in a diseased vessel. The balloon is then inflated and the restriction in the vessel is opened.

A more recent technique for treating intravascular diseases includes the use of a balloon dilatation catheter to carry and place a stent within the lumen of the blood vessel at a stenosed area. The stent is a generally cylindrical body with a lumen therethrough which is balloon-expanded when placed at the site of a lesion from a compressed configuration to an expanded configuration which physically prevents the blood vessel lumen from blocking over the length of the stent. The wall of the stent is preferably made from a metallic material and includes a pattern of interconnected struts with interstitial spaces therebetween which are open through the cylindrical wall. Stents of this design are disclosed in U.S. Pat. No. 5,449,373, and in PCT publication WO 96/03092, the disclosures of which are incorporated herein by reference. Catheters specifically designed to deliver such stents are disclosed in U.S. Pat. No. 4,950,227, the disclosure of which is also incorporated herein by reference.

There are two basic types of balloon catheters used in combination with a guide wire, namely, over-the-wire (OTW) catheters and single-operator-exchange (SOE) catheters. The construction and use of both OTW catheters and SOE catheters are well-known in the art. An example of an OTW catheter may be found in commonly-assigned U.S. Pat. No. 5,047,045 to Arney et al., the disclosure of which is incorporated herein by reference. An example of an SOE balloon catheter is disclosed in commonly-assigned U.S. Pat. No. 5,156,594 to Keith, the disclosure of which is incorporated herein by reference.

PTA and PTCA catheters are preferably designed to optimize pushability, trackability and crossability. Pushability is defined as the ability to transmit force from the proximal end of the catheter to the distal end of the catheter. Trackability is defined as the ability to navigate tortuous vasculature. Crossability is defined as the ability to navigate the balloon catheter across narrow restrictions in the vasculature.

The trackability of a particular catheter design is analyzed in terms of the trackability of the distal portion of the catheter, as this portion must track the guide wire through small tortuous vessels to reach the stenosed area to be treated. A more flexible distal portion has been found to improve trackability. Further, in transitioning from a stiff proximal segment or portion of the catheter shaft to a more flexible distal portion of the catheter shaft, it has been found that kinking readily occurs at the joint between the two shaft segments of differing flexibility. The increased flexibility of the distal section also makes this portion of the catheter less able to be pushed from the proximal end of the catheter.

The crossability is related to the trackability of a particular catheter design in that crossability is affected by the flexibility of the distal section of the catheter. Further, however, the crossability of the catheter in the area of a tight lesion is effected by the design of the distal tip of the catheter. The distal tip includes that region distal of the balloon which tracks the guide wire and at the distal-most portion that portion which first must pass through a stenosed area. Thus, much effort has gone into designing tips with improved crossability such as those disclosed in co-pending application Ser. No. 08/950,864, filed on Oct. 15, 1997 and entitled "OVER-THE-WIRE CATHETER WITH IMPROVED TRACKABILITY", the disclosure of which is incorporated herein by reference.

Although the above-referenced tip designs improve trackability and crossability, it has been found that these tip designs can be detrimental to the procedures utilized in placing and expanding a stent. More specifically, in the initial placement of a stent, the stent is preloaded over the deflated balloon and the improved tip designs actually help in getting the stent in place across a lesion because the tip provides a leading edge through the lesion. However, it is common procedure to then expand the stent by inflating the balloon followed by deflation of the balloon. The balloon catheter is then pulled back a distance over the guide wire and the placement of the stent evaluated under fluoroscopy. It is many times necessary to again move the balloon distally across the stent to perform a post or subsequent inflation of the balloon within the stent to properly seat the stent against the vessel wall. In these instances, the balloon catheter must be moved distally over the guide wire to position the balloon across the stent. In these situations, the tip must first pass through the interior of the stent. It has been found that tips incorporating designs which improve the crossability of the balloon catheter over a lesion can get caught on the struts of the stent when passing therethrough and make it difficult to post dilate the stent. This is particularly true in a bend where the leading edge of the tip catches the outside wall of the curve because the guide wire tends to be pressed against the outside radius of the curve while the distal-most tip of the catheter is biased that same direction as it attempts to follow the curve.

The above described problems associated with tip designs which are optimal for crossability of a lesion, but detrimental to crossing a stent are also prevalent in subsequent treatment of lesions that are distal of a stent within the same artery. To dilate a more distal lesion, the balloon dilatation catheter to be utilized must first pass through the lumen of a stent if one had been previously placed in the artery. The same problems with the tip catching on struts can occur.

Therefore, there is an unmet need for a catheter design which incorporates a tip which is designed for crossing lesions but which is also capable of being converted or modified to a second configuration which is suitable for crossing through the interior lumen of a stent without getting caught on a strut. The present invention, provides such a tip design or tip design in combination with a guide wire design which includes means for reconfiguring the distal-most portion of a catheter to prevent strut and tip interaction which is detrimental to crossing through the lumen of the stent.

SUMMARY OF THE INVENTION

The present invention is directed to a catheter assembly having a therapeutic device mounted proximate a distal end thereof for intravascular treatment of the vessel at a location in the lumen therein. A preferred embodiment includes an over-the-wire balloon catheter, which is described in detail herein, however, the balloon dilatation catheter can include any known type of balloon catheter including a fixed wire catheter or a single operator exchange catheter. Further, the therapeutic device mounted proximate the distal end of the catheter disclosed herein is an inflatable balloon, however, any other known therapeutic device can be mounted on the catheter and embody the invention disclosed herein.

The over-the-wire balloon dilatation catheter generally includes an elongate tubular member having a proximal end and a distal end with a guide wire receiving lumen extending therethrough. The elongate tubular member is coaxially disposed within an outer tubular member which also extends over a portion of the inner tubular member over a portion of its length. The inner tubular member extends distally beyond the outer tubular member, and an inflation lumen is formed in the annular space between the two tubular members. A balloon having a proximal end and a distal end is mounted proximate the distal end of the catheter and forms an internal volume therein in fluid communication with the inflation lumen. In preferred embodiments, the proximal end of the balloon is sealingly mounted proximate the distal end of the outer tubular member and extends distally to a distal end which is sealingly connected to the outside of the inner tubular member which extends beyond the outer tubular member. The proximal end of the catheter includes a hub assembly which provides a guide wire receiving port which goes into the lumen of the inner elongate tubular member and an inflation port which is in fluid communication with the annular inflation lumen.

The catheter includes a tip portion which, in preferred embodiments, is that portion of the catheter distal of the balloon and is generally formed by a portion of the inner tubular member having the guide wire lumen extending therethrough. The tip is designed to initially be optimum for aiding the catheter in tracking the guide wire and assisting in crossing a lesion to be dilated. Thus, the flexibility and shape of the tip are modified to aid in crossing. For example, the tip may be necked down relative to the proximal diameter of the inner or may be conically shaped having a decreasing outside diameter distally to readily penetrate an obstructed vessel.

The various embodiments of the present invention are directed to tip designs and tip and guide wire designs which, in a first configuration, are optimal for crossing a lesion. A tip or tip and guide wire combination in a second configuration is optimal for crossing a placed stent in that the tip portion does not catch on the struts in a stent, particularly a stent placed in a bend of a vessel.

In a first series of embodiments, the tip assembly includes means for reconfiguring the catheter tip from a first configuration for crossing an obstruction in the vessel lumen to a second configuration for crossing a placed stent. One embodiment includes a severable distal tip section, which is removed after treating the obstruction, but leaves a proximal portion of the tip which is more suited for crossing a stent. The remaining portion of the tip may be more bulbous in cross section or have a larger lumen that is used in conjunction with a larger guide wire.

In an alternative embodiment, the distal-most tip can be reconfigured by rolling the distal-most portion back onto the inner tubular member so that in a first configuration the tip may be passed through a lesion or obstruction, but in the second configuration, the folded back portion forms a more bulbous tip which will not catch on a strut as readily. Alternatively, the tip portion may be changeable from a straight configuration to a bent configuration which aids in crossing the stent when in a bent configuration.

In another embodiment, the inner tubular member may be slidable within the catheter or a sheath may be utilized which, when extended, provides a tip which readily crosses a lesion, but when retracted, the remaining tip portion is more bulbous or blunt for reducing the likelihood that this tip catches on the strut of a stent.

Finally, the tip of the catheter may include a distal-most portion which is rotatably secured to the inner tubular member and extends distal of the balloon. The inside lumen of the rotatably secured tip can include at least one helical protrusion on the lumen of the tip. When the catheter is moved relative to the guide wire therethrough, friction between the helical protrusion and the guide wire rotates the tip which decreases the likelihood that such tip will become caught on a strut of a stent.

In a second series of embodiments, the configuration of the guide wire utilized in conjunction with the catheter tip assembly is shaped to prevent the distal tip of the catheter from catching on the stent strut when the guide wire is selectively positioned relative to the tip, wherein it deflects or pulls the tip away from the strut while maintaining the guide wire in contact with the stent. This can include designing the guide wire with a preshaped bend at a select location, or with one or more helical coils which would be positioned within the inner lumen of the stent as the catheter crossed the stent. Alternatively, the guide wire can include a bulbous portion which, in a retracted portion, provides a more bulbous cross section on the distal tip to prevent the catheter tip from catching on a stent strut.

In another alternative embodiment, the guide wire can be caused to vibrate from the proximal end of the catheter so that the portion of the guide wire distal of the balloon vibrates in a preselected pattern which assists in preventing or deflecting a catheter tip which may get caught on a stent strut.

The distal tip of the catheter may be designed with an inflatable cuff surrounding a distal portion of the tip. The cuff can be in fluid communication with the guide wire lumen through a hole in the wall of the tip. Fluid may be injected down the guide wire lumen with sufficient pressure drop across the guide wire through the tip so that a portion of the inflation fluid fills the cuff and creates a more bulbous overall tip profile that would be less likely to catch on a stent strut when passing through the lumen of the stent.

The present invention can include a balloon catheter having a first balloon and a second, distal inflatable balloon or cuff disposed distal of the first balloon. The second, distal balloon can be inflated to increase the cross-sectional profile or maximum radial extent of the distal-most region. Increasing the profile of the distal-most region can act to deflect the distal-most end away from a stent interior wall or end. In one embodiment, the first balloon interior is in fluid communication with the distal balloon interior. These embodiments have the advantage of not requiring a separate inflation lumen for the distal balloon, which could otherwise require a tube or lumen extending the entire length of the catheter.

In one embodiment, a one-way valve is disposed between the first balloon and the distal balloon, acting to prevent rapid deflation of the distal balloon. In this embodiment, inflating the first balloon can also inflate the second balloon, whereupon the first balloon can be deflated, leaving the distal balloon still inflated. In another embodiment, a controllable valve is disposed in the fluid space between the first balloon and the distal balloon. The controllable valve can be opened, thereby allowing fluid to flow from the first balloon into the distal balloon. Fluid flow between the distal balloon and the first balloon can be prevented by manipulation of the same valve. One valve is switchable between a first, open position, and a second, closed position. Another valve is biased to remain in a closed position, and can be manipulated via a pull wire to remain in the open position while the pull wire is retracted. In this embodiment, releasing the pull wire allows the valve to return to its closed state.

One balloon catheter incorporating the present invention includes a distal region including a tube having walls and a lumen therethrough. The tube has a plurality of slits through the walls and is formed of a pre-stressed material, which has a first configuration having a first cross-sectional profile or maximum radial extent and a second configuration having a greater cross-sectional profile or maximum radial extent. The tube is pre-stressed so as to attain the second configuration after insertion within the body. One preferred distal region is formed of a shape memory material such as Nitinol or a shape memory polymer which, upon attaining body temperature, expands the maximum radial extent of the distal region. One catheter has a distal region including flaps disposed within longitudinal slits, with the flaps curling outward when heated by warm body fluid. One catheter has a distal-most end having slits which terminate prior to the distal end. In this embodiment, the distal-most end can be cut by the treating physician, thereby exposing the longitudinal slits and allowing the tip to expand upon exposure to warm body fluids.

One catheter, according to the present invention, includes a distal region having an inner tube and an innermost tube slidably disposed within the inner tube. The innermost tube can be affixed to the inner tube at the distal-most end. In this embodiment, the distal region has a plurality of longitudinal slits defining flaps therebetween. The innermost tube can be retracted proximally, thereby pulling the distal-most end of the innermost tube and the inner tube disposed about the innermost tube. In response thereto, the flaps disposed between the longitudinal slits bulge outward, thereby creating a greater maximum radial extent or cross-sectional profile of the distal region. The outwardly protruding distal region flaps can act to deflect the distal-most end of the catheter away from stent walls and ends.

In another embodiment of the invention, a balloon catheter is provided having a first, inner guide wire tube having a first guide wire lumen therethrough. The catheter can include a manifold having a proximal tapered region disposed within. A second, smaller, inner tube having a second, smaller guide wire lumen can also be provided. The second guide wire tube can have a proximal adapter having a taper adapted to be slidably received within the proximal region of the balloon catheter manifold. The inner tube assembly thus provided can be disposed within the first guide wire tube and manifold, thereby providing a smaller guide wire lumen. In use, the balloon catheter can be used in conjunction with a first guide wire, where a first, larger guide wire is desirable. When use of a second, smaller guide wire is desired, the first guide wire can be retracted. The inner tube assembly can then be advanced through the catheter, with the second inner tube being thus disposed within the first inner tube. With the second inner tube thus disposed, a second, smaller guide wire can be advanced through th e second inner tube and through the distal end of the balloon catheter. The second, smaller inner tube can provide improved support for the smaller guide wire and can provide improved resistance against buckling. In one embodiment, the second, smaller inner tube has a length sufficient to extend distally from the distal end of the first, surrounding tube when the second tube is fully advanced within the first tube.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 is a cross-sectional view of a catheter showing a preferred embodiment of the present invention;

FIG. 2 is a partial cross-sectional view of a preferred embodiment distal tip area of the catheter of FIG. 1, illustrating the tip formed from the inner;

FIG. 3 is a partial cross-sectional view of a second preferred embodiment of the distal tip area of the catheter of FIG. 1, illustrating the transition between the stiffer distal end of the inner tube and the more flexible distal tip;

FIG. 4 is a cross section view of FIG. 1 taken along line 4—4;

FIG. 16 is a schematic illustration of a catheter incorporating a guide wire that is vibrated from the proximal end;

FIG. 17 is a partial view which depicts an alternative guide wire configuration including a hump thereon with a tip positioned over a portion of the hump to prevent catching on the strut of a stent;

FIG. 18 is a partial cross-sectional view which depicts a guide wire configuration incorporating a bulbous distal portion on the guide wire;

FIG. 26 is a fragmentary, longitudinal, cross-sectional view of a catheter having a manifold and an inner guide wire tube; and FIG. 27 is a fragmentary, longitudinal, cross-sectional view of an innermost guide wire tube adapted to be slidably received within the inner guide wire tube and manifold of FIG. 26.

DETAILED DESCRIPTION OF THE PREFERRED EMBODIMENTS

Figure 5:
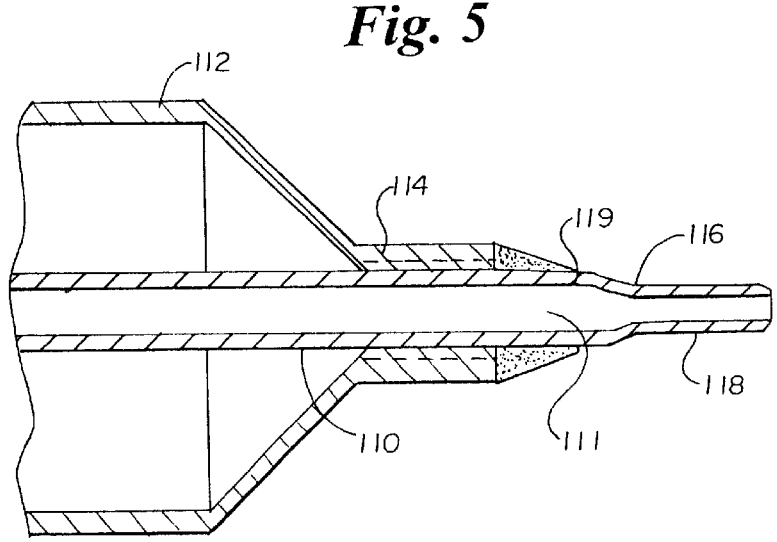
FIG. 5 is a partial cross-sectional view of a first tip design which incorporates a severable small profile distal portion and remaining blunt portion.

The following detailed description should be read with reference to the drawings in which like elements in different drawings are numbered identically. The drawings, which are not necessarily to scale, depict selected embodiments and are not intended to limit the scope of the invention.

Examples of constructions, materials, dimensions, and manufacturing processes are provided for selected elements. All other elements employ that which is known to those skilled in the field of the invention. Those skilled in the art will recognize that many of the examples provided have suitable alternatives which may also be utilized.

Referring now to the drawings, FIG. 1 is a cross-sectional view of an over-the-wire balloon catheter showing a preferred embodiment of the present invention. The balloon catheter 20 includes a shaft assembly 22 and a balloon assembly 24 connected proximate its distal end. A conventional OTW-type manifold assembly 26 is connected to the proximal end of the shaft assembly 22. The shaft assembly 22 includes an inner tube 28 having a proximal end 30 and a distal end 32. The proximal end of the shaft assembly 21 extends into the manifold assembly 26 adhesively bonded to the shaft assembly 22. A polyurethane strain relief 23 is snap-fit to the manifold assembly 26, and the shaft assembly 22 extends into the manifold assembly 26 through the polyurethane strain relief 23. An outer tube 34 is coaxially disposed about the inner tube 28 to define an annular inflation lumen 37.

The balloon assembly 24 includes a balloon body portion 36 with a proximal balloon waist 38 and a distal balloon waist 40. The proximal balloon waist 38 is connected to the outer tube 34 near its distal end by means of an adhesive 44. The distal balloon waist 40 is connected to the inner tube 28 near its distal end 32 by means of an adhesive bond 48 such that the interior of the balloon 46 is in fluid communication with the annular inflation lumen 37.

A radiopaque marker band 50 is adhesively secured with cyanoacrylate adhesive to the inner tube 28 at a point underneath the balloon body 36. Alternatively, the marker band may be swaged onto the outer surface of the inner. The inner tube 28 defines a guide wire lumen 54 which provides a passage for a guide wire (not shown). The outer tube 34 defines an annular inflation lumen 37 which is in fluid communication with the interior of the balloon 46.

As previously stated, the catheter of the present invention preferably includes an outer tube having a relatively stiff proximal outer section, a mid-shaft section of lesser stiffness, and a tapering distal outer section of the least stiffness. The progressive arrangement of more flexible materials as the catheter proceeds distally provides an optimal level of pushability and trackability to navigate tortuous vasculature. The flexibility of the segments of the outer tubular member were tested utilizing a Gurley bending resistance tester, Part No. 4171-DT, as manufactured by Precision Instruments, Troy, N.Y. The apparatus consists of a balanced pendulum or pointer which is center-pivoted and can be weighted at three points below its center. The pointer moves freely in both the left and right directions. A sample of specific size is attached to a clamp, which in turn is located in one of several positions on a motorized arm which also moves left and right. During the test, the sample is moved against the top edge of the vane, moving the pendulum until a sample bends and releases it. The test is run in two steps, first to the left and then to the right. The scale reading is measured in each direction and the results are averaged. The instrument provides a relative flexibility measurement between the components of the outer tubular member as detailed below to achieve improved trackability and pushability.

The outer tube 34 has a relatively stiff, proximal outer section 56 with a proximal end 60 and a distal end 62. The proximal outer tube may be made of nylon, a polyamide, such as DURETHANE available from Bayer, a DURETHANE braid, CRISTAMID braid or polyetheretherketone (PEEK) braid. A preferred embodiment of PEEK or CRISTAMID braid is a variable PIC tube, wherein said PIC varies from about 30 to 100 PIC to give varying flexibility over the length of the proximal outer tube. The PIC preferably varies from about 50 to about 80. The braiding material in the PEEK or DURETHANE (polymer) braid may be made from stainless steel, or Nitinol (nickel titanium alloy). This proximal outer section 56 will have an outside diameter ranging from 0.040 inches to 0.045 inches with a wall thickness ranging from 0.0028 inches to 0.0044 inches. The proximal outer section has a preferred Gurley value of about 500 to about 1300 over its length. A preferred range is about 800 to about 1200. FIG. 4 illustrates a cross section view of the proximal outer section having braid material as taken along 4—4 of FIG. 1. The braid includes an inner layer 100, a braid layer 101 and an outer layer 102.

A midshaft section 58 with a proximal end 64 and a distal end 66 extends distally from the distal end of the proximal outer section 62. The midshaft section 58 has a stiffness less than that of the proximal outer section 56. The midshaft section 58 is preferably made from a polyamide, such as CRISTAMID available from Elf Atochem, having a durometer of about 81D. A preferred Gurley value for the midsection is about 350 to about 500, with a range of 400 to 450 preferred. This midshaft section 58 will have an outside diameter ranging from 0.040 inches to 0.045 inches with a wall thickness ranging from 0.0028 inches to 0.0044 inches.

The distal end of the proximal outer section 62 is joined to the proximal end of the midshaft section 64 with a urethane adhesive bond or a thermal weld. A distal outer section 68 having a proximal end 70 and a distal end 72 extends distally from the distal end of the midshaft section 66 to the distal end of the outer tube 44. This distal outer section 68 is more flexible or has less stiffness than both the proximal outer section 56 and the midshaft section 58. The outer diameter of the distal outer section 68 will taper from about 0.045 inches at the proximal end 70 to 0.030 inches at the distal end 72. This distal outer section 68 is made of polyether block amide (PEBAX) with a durometer of 70D. The tapered distal outer section preferably has a Gurley value of about 70 to about 90 at its proximal end and about 15 to about 40 at its distal end. Thus, the distal end of the distal outer section 72 will exhibit less stiffness than the proximal end of the distal outer section 70. The distal end of the midshaft section 66 is joined to the proximal end of the distal outer section 70 with a urethane adhesive bond or a thermal weld.

A Nitinol braid insert 74 with a length of about 1.0" is placed within the proximal end of the distal outer section 70 to provide strain relief and reduce kinkability at the midshaft/distal outer section junction. This Nitinol braid 74 has a 0.001"x0.005" ribbon.

The inner tube 28 is made of polyethylene such as Marlex HDPE. At the proximal end of the inner tube 30, the inner tube 28 has an outside diameter ranging from 0.024 inches to 0.026 inches and preferably about 0.025 inches, with the inner tube 28 having an inside diameter ranging from 0.018 inches to 0.0195 inches for a 0.014 inch guide wire for which this lumen is designed to be compatible with. The inner tube 28 has a wall thickness ranging from 0.0026 inches to 0.004 inches and preferably about 0.0032 inches. The outside diameter to wall thickness ratio must be sufficiently small to minimize the propensity of kinking.

As the inner tube 28 extends distally through the junction area between the distal end of the proximal outer section 62 and the proximal end of the midshaft section 64 of the outer tube 28, both the inner and outer diameters of the inner tube 28 will taper from wider diameters to narrower diameters. Likewise, at the distal end of the inner tube 32, both the inner and outer diameters of the inner tube 28 will once again taper from wider diameters to narrower diameters as the tube extends distally.

As illustrated in FIG. 2, in one preferred embodiment, a distal tip 76 is formed on the distal end of the inner tube 32 where the inner tube 28 distally tapers from a larger outer diameter to a smaller outer diameter. The distal balloon waist 40 is attached to the distal tip 76 through a urethane adhesive bond at a bonding area. The area just distal of the distal waist bond is backfilled with adhesive 43 to provide a smooth transition. The adhesive coating provides for improved adhesion between dissimilar substrates.

The proximal catheter shaft portion is preferably about 35 to 45 inches in length with a preferred length of 42 inches. The midshaft section is preferably about 1 to about 3 inches in length with a preferred length of 2 inches. The distal outer section having the most flexibility is preferably about 8 to about 12 inches in length with a preferred length of about 10 inches.

In another preferred embodiment, as shown in FIG. 3, a polyethylene distal tip 80 of durometer between about 45D and 65D, preferably about 55D is heat welded or bonded to the distal end of the inner tube 32 with a durometer of about 63–65D, and the distal balloon waist 40 of the balloon is adhesively bonded to both the inner and the tip extending therefrom. As shown in FIG. 3, the joint 41 between the inner and the tip is located under the distal waist of the balloon. The outer diameter of the polyethylene distal tip 80 distally tapers from a larger outer diameter to a smaller outer diameter.

In another preferred embodiment, incorporating a soft tip as described above, the last ½ to 1 mm of the tip at its distal end is made of a different material from the tip material to form a tip extension. In particular, the last ½ to 1 mm is made from a material which is more durable relative to the softer tip material. In particular, the more durable material will resist deforming or tearing when in use, such as tracking tortuous anatomy or through a placed stent. For example, this last ½ to 1 mm may be manufactured from Marlex high density polyethylene having a 63D durometer which improves the integrity of the tip portion at its distal-most end 81.

As previously discussed with respect to FIGS. 2 and 3, the tip design of the present catheter includes features which assist in the tip portion of the balloon catheter crossing a lesion or obstruction in a lumen. This can include a conically shaped tip which reduces an outside diameter, or has an area of reduced outside diameter. This can also include utilizing materials which are relatively soft to improve the trackability. These designs, however, are not optimum for the tip to cross through the inside lumen of a stent having struts thereon. The tip, as depicted in FIGS. 2 and 3, tend to catch on the struts of the stent, particularly if the guide wire that the tip is tracking is in a curve or bend in the vessel lumen. In such bend, the tracking tip tends to bias toward the outward edge of the bend where it can readily catch on the stent strut. The present disclosure is directed to tip and tip and guide wire combination designs which include means for reconfiguring the catheter tip so that it more readily crosses a placed stent.

Referring now to FIG. 5, a first embodiment incorporating a means for reconfiguring the distal tip of the catheter from a first configuration for crossing vessel lumen obstructions to a second configurations for crossing a placed stent is depicted. The embodiment disclosed includes an inner tubular member 110 extending through a balloon 112 having a distal waist 114. The tubular member 110 extends distally through the balloon waist 114 and protrudes distally therefrom to form a tip 116. The tubular member 110 has a lumen 111 extending therethrough for receiving a guide wire (not shown). The tip 116 includes a distal portion 118 having a reduced inside and outside diameter relative to the proximal portion of the tubular member 110. In a first configuration for crossing a vessel lumen obstruction, the tip is configured as depicted in FIG. 5. To reconfigure the tip for crossing a stent, the tip is severed proximal of the necked down portion of the tip 118, as for example, at 119. To facilitate removal of a portion of the tip, a line of weakened strength can be included, such as a perforation to aid in removing such portion. In the second configuration, the distal-most portion of the inner tubular member 110 is a distal end 119, which as depicted in FIG. 5, is of greater cross section and more blunt than the prior configuration. This aids in passing by the struts of the stent and can be further assisted by using a larger diameter guide wire which provides additional stiffness through the stent lumen.

In a preferred embodiment of the tip of FIG. 5, the severable tip 118 has a reduced lumen diameter, preferably sized for use with a guide wire having a diameter of 0.014 inches, while the lumen proximal thereof has a diameter sized for use with a 0.018 inch guide wire. This option is useful even in non-stent crossing applications, for example, any time a stiffer wire is necessary.

Figure 6:
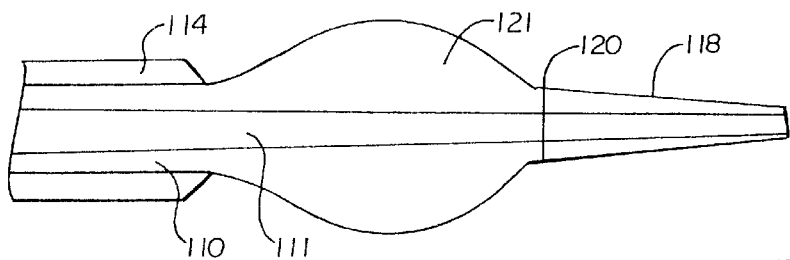
FIG. 6 is a partial cross-sectional view of an alternative embodiment similar to that of FIG. 5 which incorporates a severable conical tip portion with a remaining bulbous proximal tip portion.

Referring now to FIG. 6, an alternative embodiment of the tip design of FIG. 5 is depicted. With this design, the balloon also includes proximal waist 114 and inner tubular member 110 extending therethrough. A guide wire lumen 111 runs through the inner tubular member 110. In a first configuration, the tip design of FIG. 6 includes a distal tip portion 118 which is generally conical along the outside diameter for more readily penetrating an obstruction in a vessel lumen. The tip design is convertible or reconfigurable to a second configuration which more readily crosses a stent by severing the distal tip portion 118 at an area such as 120. Proximal of this point of severability, the tip includes a generally bulbous portion 121. The bulbous cross section of the remaining tip portion is designed to pass over a stent strut without catching the leading edge.

Figure 7:
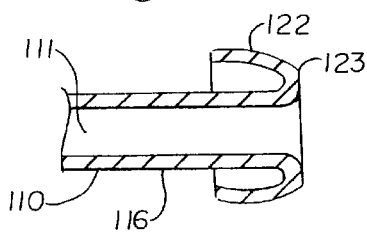
FIG. 7 is a partial cross-sectional view of a tip design embodiment which incorporates a distal-most portion which folds back onto the tip to form a more bulbous cross section.

Referring now to FIG. 7, a cross section of a distal-most portion of the inner tubular member forming the tip 116 is depicted with the guide wire receiving lumen 111 extending therethrough. With this embodiment, the means for reconfiguring the catheter tip comprises a soft distal-most tip portion 122 which is configured to roll back onto the inner tubular member 116 at its distal-most end to form a bulbous leading edge 123 that aids in crossing a stent without catching on a strut. The distal-most tip portion 122 can be skived longitudinally to aid in rolling back the tip when in contact with a stent.

Figure 8:
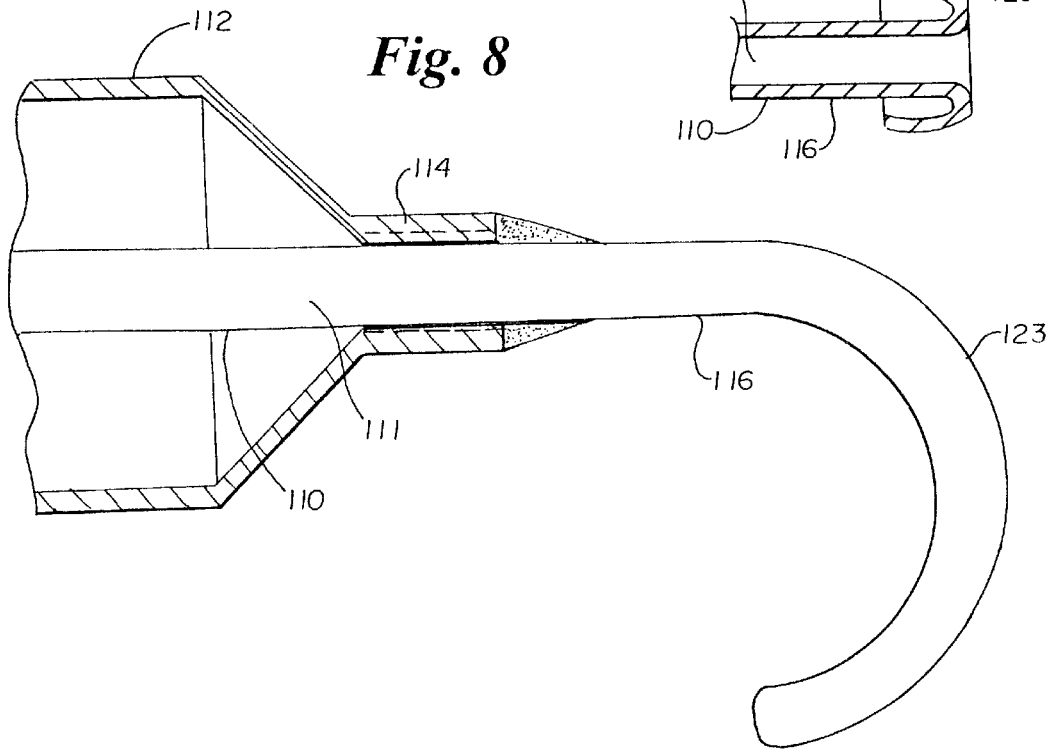
FIG. 8 is a partial cross-sectional view of a tip design which is deflectable to a curved configuration to aid in crossing a placed stent.

Referring now to FIG. 8, another alternative embodiment incorporating means for reconfiguring the catheter tip is disclosed. The embodiment of FIG. 8 includes an inner tubular member 110 having a lumen 111 extending therethrough for receiving a guide wire. A tip 116 is formed distal of the distal waist 114 of the balloon 112. With this embodiment, a first configuration, not shown, would include a straight tip 116 when the guide wire is extended therethrough. The guide wire can then be retracted proximally and the tip can be prebiased to reconfigure to a bent configuration such as that depicted in FIG. 8. The blunt end 123 of the bent section of the tip more readily crosses a stent without catching on a strut since the leading edge of the tip is no longer able to contact the strut and catch thereon.

Figure 9:
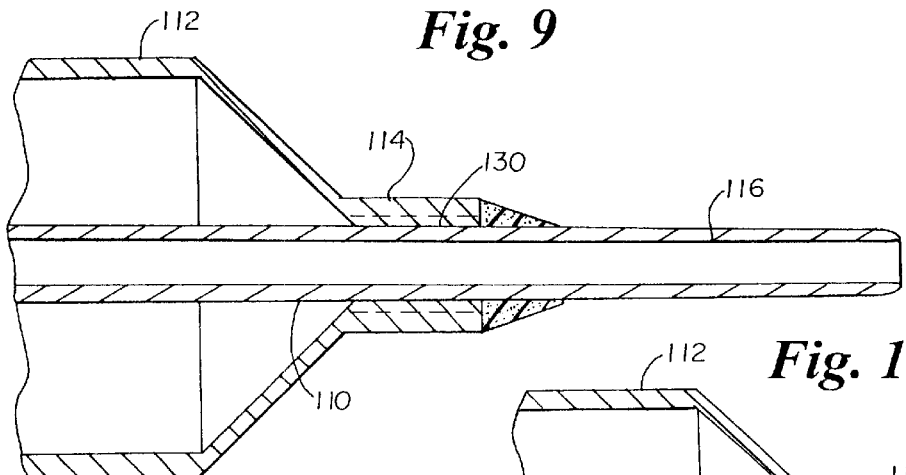
FIG. 9 is a partial cross-sectional view of a tip design incorporating an inner tubular member which is extendable to an extended position which aids in crossing a lesion.
Figure 10:
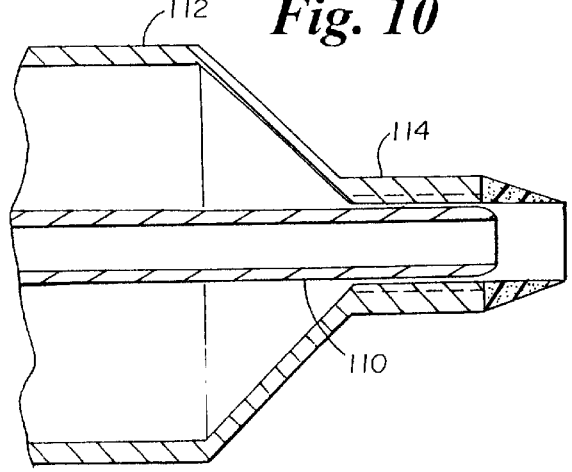
FIG. 10 is a partial cross-sectional view of the tip design of FIG. 9 with the tubular member in a retracted position which leaves a blunter profile for crossing a placed stent.

Referring now to FIGS. 9 and 10, another alternative embodiment of a tip design is disclosed. With the tip design of FIGS. 9 and 10, the means for reconfiguring the catheter tip include an inner tubular member 110 extending through the balloon 112 and distal waist 114. However, the outside surface of the inner tubular member is not adhesively secured to the distal waist of the balloon, but rather slidably received therethrough. In a first configuration, as depicted in FIG. 9, the inner tubular member 110 is extended distally to form the tip 116 which is suitable for crossing an obstructed lumen. FIG. 10 depicts the embodiment of FIG. 9 in the reconfigured mode, wherein the inner tubular member 110 is retracted proximally to leave a more blunt profile on the distal-most portion of the catheter which aids in crossing a stent. In order for the inner tubular member 110 to be utilized in the above-described manner, the area of engagement 130 of the balloon waist 114 with the exterior surface of the inner tubular member 110 must form a seal therebetween so that the inflation fluid does not substantially leak therethrough. This can be accomplished based on tolerances or prebiasing the distal waist of the balloon. Alternatively, an O-ring type seal could be included in the distal waist of the balloon or on the exterior surface of the inner tubular member as positioned under the distal waist of the balloon.

Figure 11:
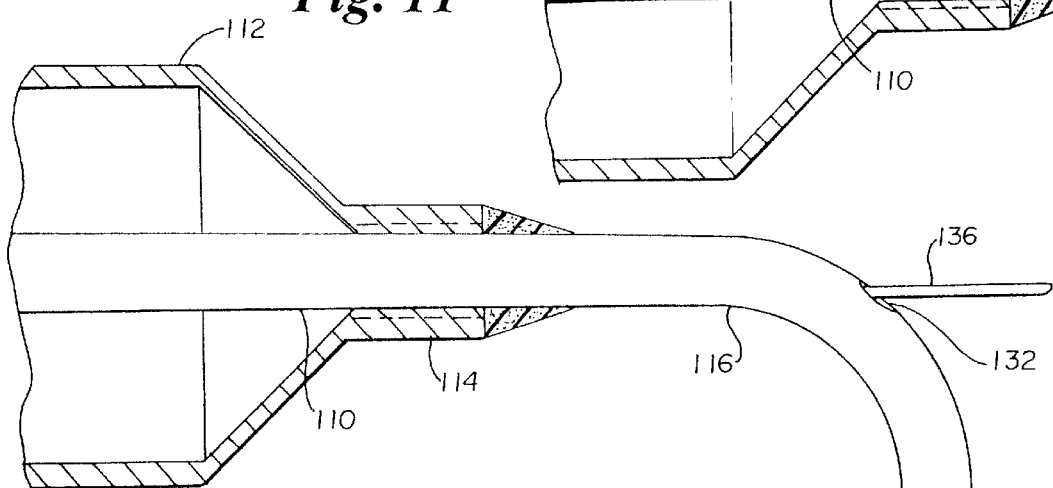
FIG. 11 is a partial cross-sectional view of a tip design including a hole through the wall thereof so that in a first configuration the tip is straight with the guide wire extending through the distal end thereof, while in a second configuration the guide wire protrudes distally through the hole creating a bent distal tip portion for crossing a stent.

Referring now to FIG. 11, another alternative embodiment of a distal tip design is depicted. In the embodiment of FIG. 11, the inner tubular member 110 includes a distal portion 116 which extends beyond the distal waist 114 of the balloon 112. The portion of the inner tubular member extending beyond the distal waist forms the tip. The tip of this embodiment includes a hole 132 through the side wall at a position proximal of the distal-most end 134 of the tip 116. In a first configuration, which is not shown in FIG. 11, the guide wire 136 extends through the distal end of the tip 116 and holds the tip portion in a straight configuration which is more suitable for crossing an obstruction in a lumen. The tip is reconfigured by passing the guide wire through the hole 132 in the side wall so that the portion of the tip distal of the hole forms a bent configuration which more readily crosses a placed stent.

Figure 12:
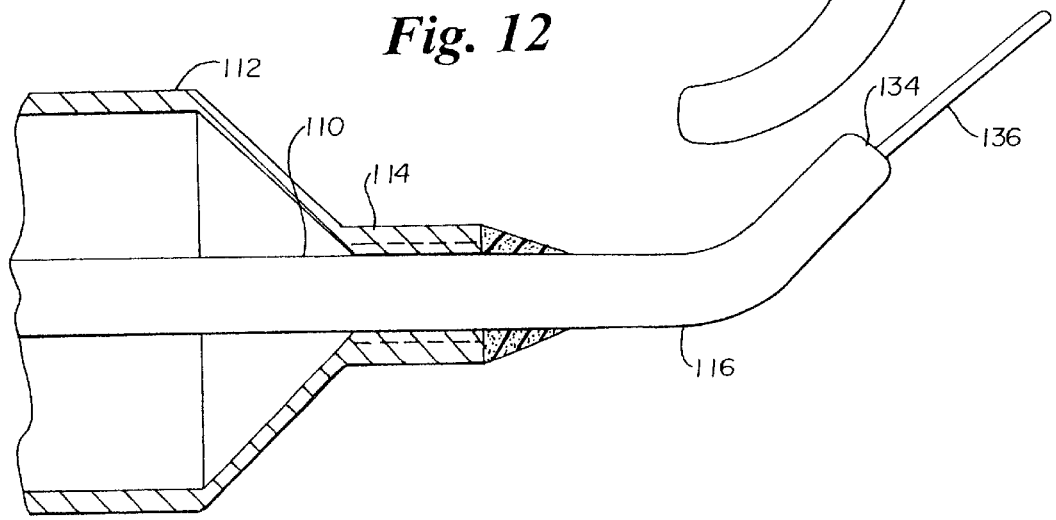
FIG. 12 is a partial cross-sectional view which depicts an alternative tip design incorporating a bendable distal tip portion which in a bent position as depicted aids in crossing a stent by rotating the catheter.

Referring now to FIG. 12, an alternative embodiment of a distal tip 116 is depicted. With the embodiment of FIG. 12, the distal tip 116 is first configured as a straight tip having a guide wire extending therethrough. The tip is designed to be reconfigured to a bent tip which is bent with an acute angle from straight, as for example, a 45° angle from straight. The tip is designed to be held at this angle, as for example by incorporating metal strips or a coil or braid which remains reconfigured when bent. With the tip bent at an acute angle from straight, the tip is configured for crossing a stent, in that if resistance to moving distally is encountered in the stent, the catheter can be rotated from the proximal end so that the distal-most tip 134 deflects away from the stent wall and should proceed through the stent as rotated. The stent will then contact a portion of the tip 116 which is proximal of the distal-most tip 134.

Figure 15:
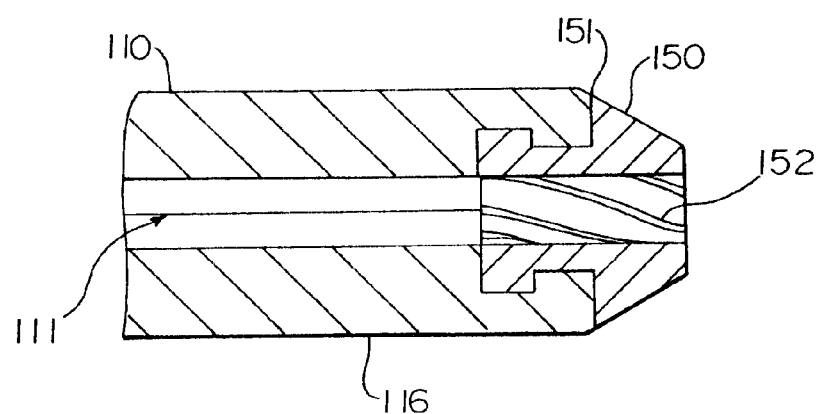
FIG. 15 is a partial cross-sectional view which depicts a catheter tip design incorporating a rotatably secured distal-most portion which is rotated in conjunction with friction along the guide wire.

Referring now to FIG. 15, another alternative embodiment of a tip configuration is depicted. The tip 116 of inner elongate tubular member 110 includes a distal-most portion 150 rotatably secured to the distal end 151 of the inner elongate tubular member 110. The distal-most portion 115 is configured to rotate in response to axial movement of the elongate tubular member 110 relative to a guide wire placed in the lumen 111 therethrough. In a preferred embodiment, the lumen of the distal-most tip portion 150 includes at least one helical projection 152 therein which causes the rotational movement of the distal-most tip portion 115 due to friction with the guide wire when moved axially relative thereto. The slight rotation of the tip as it passes through the lumen of the stent is believed to aid in preventing the distal-most tip portion from catching on a stent strut while not being detrimental to the tip's ability to cross a lumen obstruction.

Figure 20:
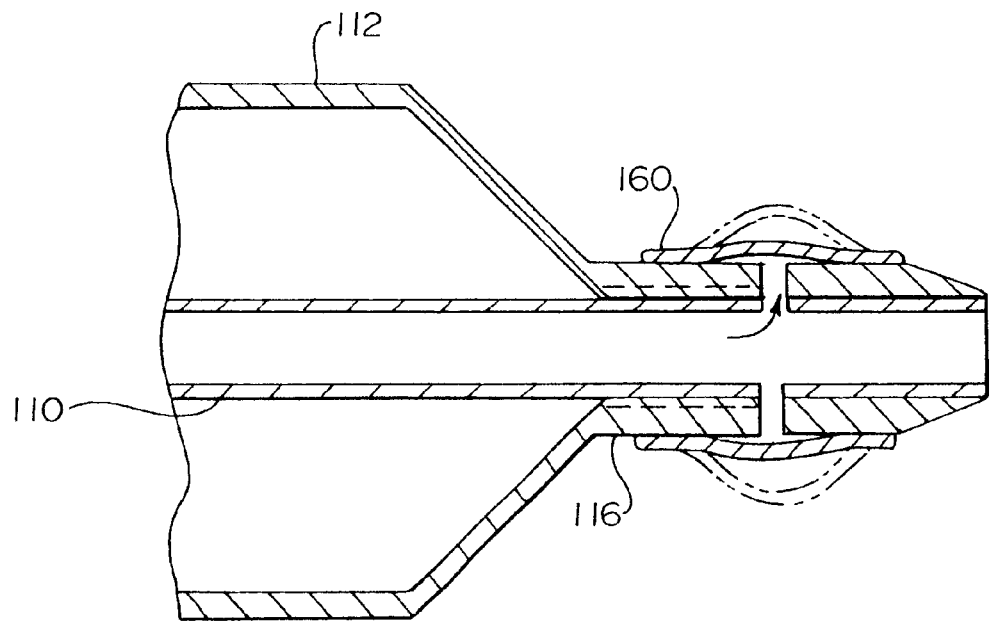
FIG. 20 is a partial cross-sectional view which depicts a tip configuration incorporating an inflatable cuff which inflates to provide a generally bulbous profile that is less likely to catch on a stent.

Referring now to FIG. 20, another alternative embodiment of altering the tip configuration on the catheter assembly is disclosed. The embodiment of FIG. 20 includes an inflatable cuff 160 which is secured to the outside diameter of the distal tip portion 116. The cuff is inflatable from a first position wherein the cuff is flat on the outside diameter of the tip 116 to an inflated position which forms a more bulbous profile which is more adequate for crossing a stent. The tip in both configurations is depicted in FIG. 20. The cuff may be inflated or expanded via a hole through the wall of the tip 116 by passing fluid down the guide wire lumen with the guide wire therein. The guide wire can be sized, especially in the distal portion, so that the resistance to fluid flow out the distal end of the catheter forces some of the fluid into the expandable cuff 160.

Referring now to FIGS. 13, 14 and 16–19, another type of tip and guide wire design is disclosed which incorporates a guide wire having means for deflecting the tip away from the interior wall of the stent to aid in passing through the lumen of the stent. By deflecting the distal-most or leading edge of the tip, away from the stent wall, catching on struts is prevented. Each of the various embodiments discussed below function in this manner.

Figure 13:
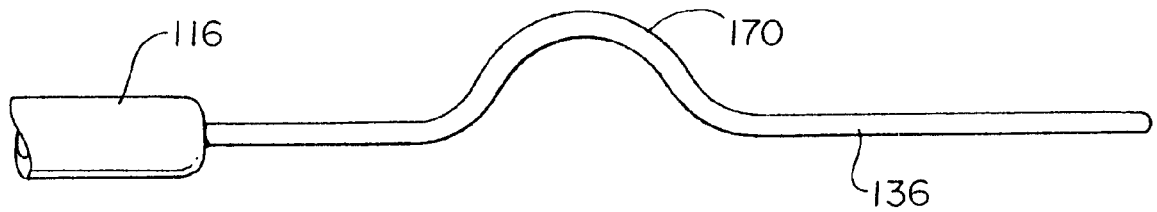
FIG. 13 is a partial cross-sectional view which depicts a guide wire configuration incorporating an offset bend or hump which contacts the wall of a stent and deflects the tip away therefrom.

Referring now to FIG. 13, a guide wire 136 is depicted extending distally from the distal tip 116. The guide wire has preformed therein an offset or hump 170. The distal tip 116 can be positioned just proximal of the offset 170 so that when the tip and guide wire are moved together around a bend in a vessel which contains a stent therein, the hump 170 contacts the stent wall and deflects the tip 116 away from the struts.

In an alternative mode of operation, as depicted in FIG. 17, the guide wire also includes a hump or bend 170. However, with this embodiment, the tip 116 is positioned so that a distal-most portion 172 is positioned partway around the bend or hump 170. As shown in FIG. 17, this forms a bend in the distal end of the tip 116 which, when moved distally together with the guide wire, would not contact the struts on a stent. Although a single hump or bend is depicted, it is recognized that multiple humps or bends can be included in the same or differing planes.

Figure 14:
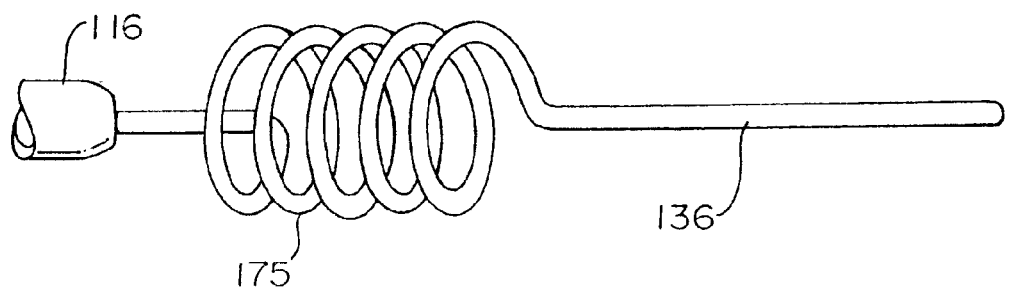
FIG. 14 is a partial cross-sectional view which depicts a guide wire configuration incorporating multiple coils which deflect the tip away from a placed stent when the tip is crossing over such coils.

Referring now to FIG. 14, another alternative guide wire design incorporating means to deflect the tip away from the stent wall is depicted. The guide wire 136 includes a plurality of helical coils 175. The outside diameter of the helical coils is greater than the diameter of the guide wire lumen so that the tip 116 is deflected away from the stent wall when both are moved distally through a stent lumen. Alternatively, the coils can be designed so that they straighten in response to the tip passing thereover. When straightening the coils, the tip will be deflected with each pass based upon the bias of the coil and will deflect the tip away from the stent wall. With this embodiment, the coiled portion of the guide wire would generally include a length which is equal to or greater than the length of the stent through which the catheter must pass.

Referring now to FIG. 16, the catheter 20 of FIG. 1 is depicted schematically. The catheter includes a tip 116 and a guide wire 136 which extends distally beyond the distal end of the tip. Means for imparting vibration 180 is included on the proximal end of the catheter and connected to the guide wire. By imparting vibration to the guide wire, it is believed that the distal end of the guide wire will vibrate as the catheter tip 116 passes thereover. The vibrational pattern is depicted in phantom 138 in FIG. 16. It is believed this vibration will cause the catheter tip 116 to deflect away from the stent wall 140 as depicted.

Figure 19:
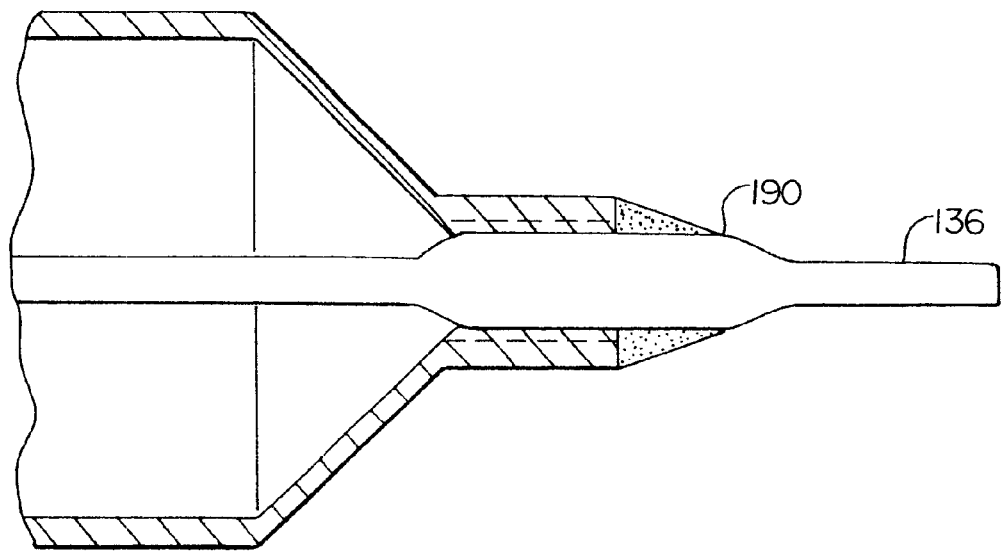
FIG. 19 is a partial cross-sectional view which depicts the guide wire assembly of FIG. 18 in a retracted position which includes a tight tolerance with the bulbous portion which prevents the catheter tip from catching on a stent strut.

Another guide wire embodiment is depicted in FIGS. 18 and 19. The guide wire 136 includes a portion of expanded diameter 190. In an extended position, the gap between the guide wire lumen and the outside surface of the guide wire allows for easy tracking of the guide wire thereover. As depicted in FIG. 19, when the guide wire 136 is in a retracted position, the tolerance between the guide wire lumen and the expanded portion 190 of the guide wire 136 is extremely tight tolerance so that the tip does not fit loosely on the guide wire. This will cause the tip to more closely track the guide wire and prevent it from deflecting and catching on a stent strut.

Figure 21:
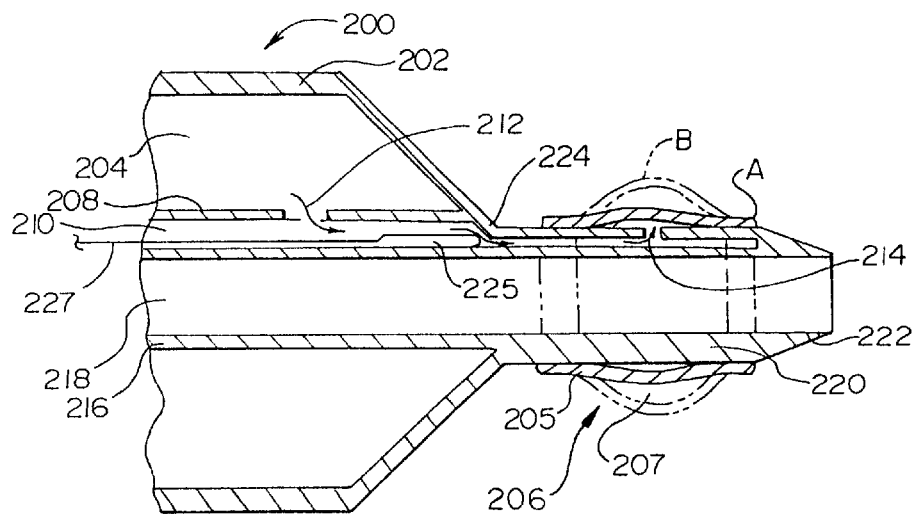
FIG. 21 is a fragmentary, longitudinal, cross-sectional view of a catheter distal portion having an inflatable bulbous tip.

Referring now to FIG. 21, a balloon assembly 200 is illustrated, including a balloon body 202 a distal tip 220, and a distal-most end 222. Balloon assembly 200 further includes a distal inflatable cuff or balloon 206 including a balloon wall or envelope 205 and a balloon interior 207. Distal balloon 206 has a first, uninflated configuration indicated at A, and a second, inflated configuration indicated at B. In one embodiment, distal inflatable balloon 206 imparts a bulbous shape to distal tip 220. Balloon 206 can be formed from balloon envelope material adhered to the distal tip region. Balloon body 202 includes a balloon interior 204, and in the embodiment shown, a balloon interior wall 208. Balloon assembly 200 includes a distal balloon inflation lumen 210 and a guide wire lumen 218 defined by an inner tube 216. In the embodiment illustrated, balloon interior 204 is in communication with distal balloon inflation lumen 210 through a first opening 212, and distal balloon inflation lumen 210 is in communication with distal inflatable balloon interior 207 through a second opening 214. In one embodiment, distal balloon inflation lumen 210 is defined by a tube extending through balloon body 202 and including, for example, balloon interior wall 208. In one embodiment, balloon body 202 interior 204 is in fluid communication with distal inflatable balloon 206, such that inflating balloon 202 inflates distal inflatable balloon 206.

In one embodiment, a valve acts to allow inflation of distal inflatable balloon 206 while inflation fluid is provided under pressure, yet does not allow exit of inflation fluid from distal inflatable balloon 206 in the absence of inflation fluid pressure. In the embodiment illustrated in FIG. 21, a valve plug 225 is disposed at the distal end of a valve control wire 227 and positioned near a valve seat 224. Valve plug 225 can be retracted to allow fluid flow from balloon interior 204 into distal balloon interior 206. Valve plug 225 can be advanced against valve seat 224 to prevent fluid flow between balloons 202 and 206. In one embodiment, valve plug 225 is distally biased, for example with a spring, to seat against valve seat 224. Valve plug 225, when retracted, allows balloon 202 to be inflated substantially simultaneously with distal balloon 206. Valve plug 225, when seated, allows balloon 202 to be deflated while distal balloon 206 remains inflated.

In one embodiment, a one-way valve allows infusion of inflation fluid under pressure into distal inflatable balloon 206, yet allows only gradual deflation of distal inflatable balloon 206, back through the one-way valve. In the aforementioned embodiment, the valve termed a one-way valve can actually allow flow in a second direction, albeit at a much slower rate than in a first, primary direction. In one embodiment, distal inflatable balloon 206 is configured so as to allow a gradual deflation of the balloon in the absence of infusion fluid supplied under pressure.

As can be seen from inspection of FIG. 21, the bulbous shape of distal inflatable balloon 206, when inflated, can act to deflect distal-most end 222 away from the edge or interior wall of a stent.

In use, in embodiments having a separate inflation lumen for the distal inflatable balloon, the balloon assembly can be advanced near a stent. The distal inflatable balloon can be inflated to attain a larger or bulbous profile, and distal-most end 222 is then further advanced through the stent. After distal-most end 222 has been advanced sufficiently through the stent, the distal inflatable balloon can either be left inflated, deflated, or allowed to deflate at a controlled rate through a controlled deflation means such as a permeable membrane or a small escape orifice. In embodiments having a separate distal balloon inflation lumen, one method utilizes the separate inflation lumen for both inflation and deflation of the distal inflatable balloon.

In use, in embodiments having a shared fluid space between balloon body 202 and distal inflatable balloon 206, balloon body 202 and distal inflatable balloon 206 are both inflated prior to advancing distal-most end 222 into a stent to be crossed. In one method, after distal-most end 222 has been advanced sufficiently into stent, balloon body 202 and distal inflatable balloon 206 are allowed to deflate or are actively deflated by removing inflation fluid, allowing balloon body 202 to more easily enter the stent. In embodiments having a shared fluid space between balloon body 202 and distal inflatable balloon 206 and further having a one-way valve and controlled escape of inflation fluid from distal balloon 206, both balloon body 202 and distal balloon 206 can be inflated before advancing distal-most end 222 into a stent. After distal-most end 222 has been advanced sufficiently into the stent, inflation fluid pressure may be removed, allowing balloon 202 to deflate, yet allowing distal balloon 206 to remain inflated. In one method, distal balloon 206 deflates at a controlled rate by escape of inflation fluid through a means for inflation fluid escape such as a semi-permeable membrane or an escape orifice in distal balloon 206. The use of a one-way valve in the shared fluid space between balloon body 202 and distal balloon 206 can eliminate the need for a separate inflation lumen or tube extending the entire length of the catheter. This can reduce the overall profile and complexity of the catheter. In particular, use of a shared fluid space allows distal inflatable balloon 206 to be effectively inflated using fluids supplied to distal balloon 202.

Figure 22:
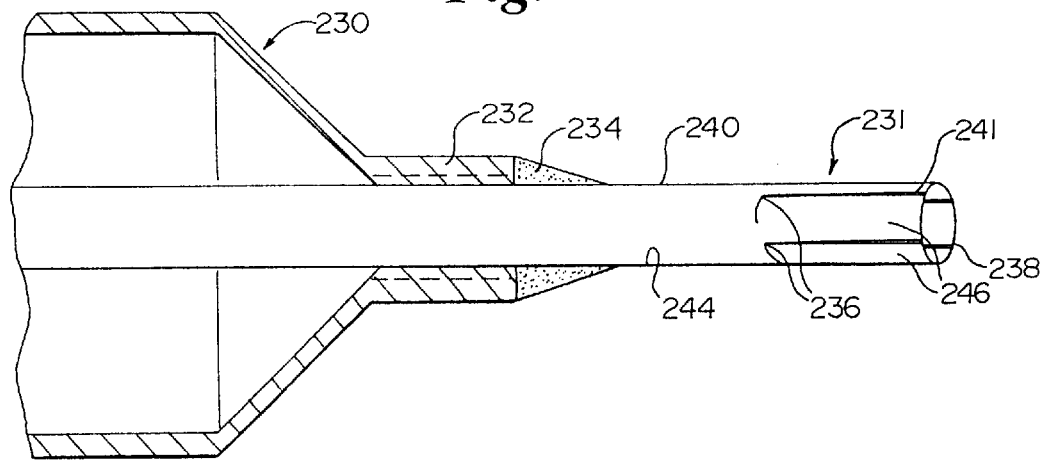
FIG. 22 is a fragmentary, longitudinal, cross-sectional view of a catheter distal portion and a perspective view of an inner tube having a pre-stressed, longitudinally slit, distal portion prior to expansion.

Referring now to FIG. 22, a balloon assembly 230 is illustrated including a balloon distal waist 232, an adhesive area 234, and an inner tube 240. Inner tube 240 includes a tube wall 244 and a distal portion 231, and terminates distally in a distal-most end 238. In the embodiment shown, a plurality of longitudinal slits 236 extend through tube wall 244 near distal-most end 238, but not through an unslit distal region 241. Slits 236 define a plurality of flaps 246 therebetween. Unslit region 241 extends distal of slits 236, allowing an unslit distal-most end to be presented. In this embodiment, unslit region 241 can be cut transversely and removed, thereby presenting slits 236 at the distal-most end. In FIG. 22, distal-most end 238 is shown in a first state having a cross-sectional profile and a radial extent substantially that of tube 244, and including unslit region 241. In one embodiment, distal portion 231 is formed of a shape memory material, such as Nitinol or a shape memory polymer well known to those in the art.

Figure 23:
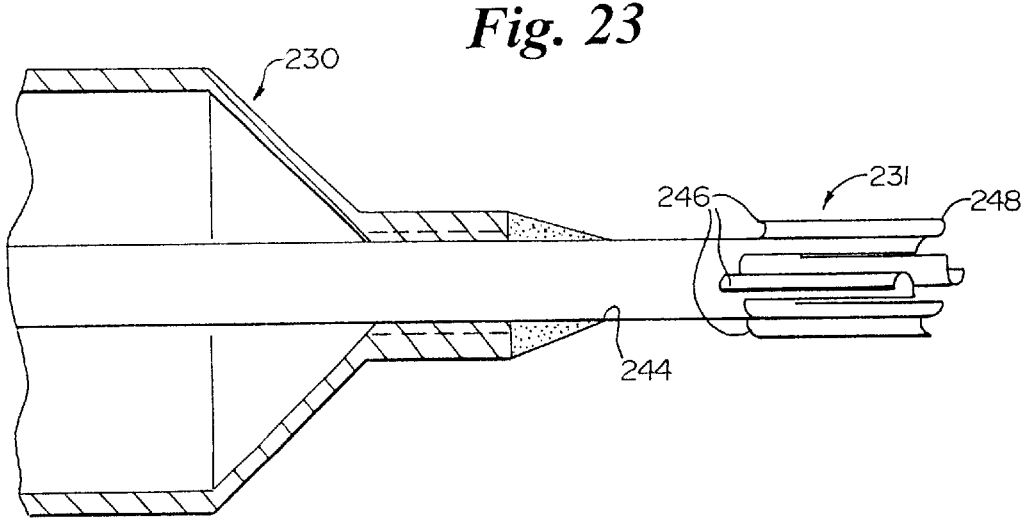
FIG. 23 is a fragmentary, longitudinal, cross-sectional view of the catheter distal portion of FIG. 22, illustrating the pre-stressed, slit distal portion after expansion.

Referring now to FIG. 23, balloon assembly 230 is shown in a second state having unslit region 241 removed and distal portion 231 having an increased cross-sectional profile and radial extent relative to distal portion 231 as shown in FIG. 22 and relative to the majority of the length of inner tube 244. FIG. 23 illustrates flaps 246 having a curled and outwardly extending configuration. Flaps 246, by having an increased radial extent relative to tube 244, present an increased distal-most profile when approaching a stent.

The increased distal-most profile presented by flaps 246 acts to prevent distal-most end 238 from catching in a stent to be crossed. The flaps 246, especially when having a number of relatively floppy or flexible corners 248, present a distal-most end having less resistance when catching on a stent. In particular, the floppy distal-most corners 248 tend to bend back toward the balloon when caught on a stent wall or edge. Thus, balloon assembly 230 can be advanced distally through a stent even when distal-most corners 248 become engaged with a stent. Similarly, the increased slit width caused by curling of flaps 246 decreases the strength of distal portion 231 relative to a distal portion having no slits. The relatively weakened distal portion as a whole thus presents a more flexible or floppy distal region when engaged with a stent wall or edge, allowing balloon assembly 230 to be further advanced distally, even when distal portion 231 is engaged. In this scenario, distal portion 231 flaps 246 are expected to bend proximally toward the balloon and then curl distally once balloon assembly 230 is further advanced, and the engagement between flaps 246 and the stent ends when the flaps are freed of the stent.

In use, in embodiments having a distal-most end that includes no slits at the distal-most end, the balloon assembly and catheter can be used in a normal fashion until difficulty in crossing a stent is encountered or expected. At this point, the catheter can be retracted and the unslit portion of distal portion 231 cut, thereby exposing a distal portion having slits extending through to the most-distal end. The catheter can then be advanced to the stent to be crossed. Flaps 246, having been formed of a shape memory material, can attain the outward configuration illustrated in FIG. 23 after sufficient exposure to body temperature.

Figure 24:
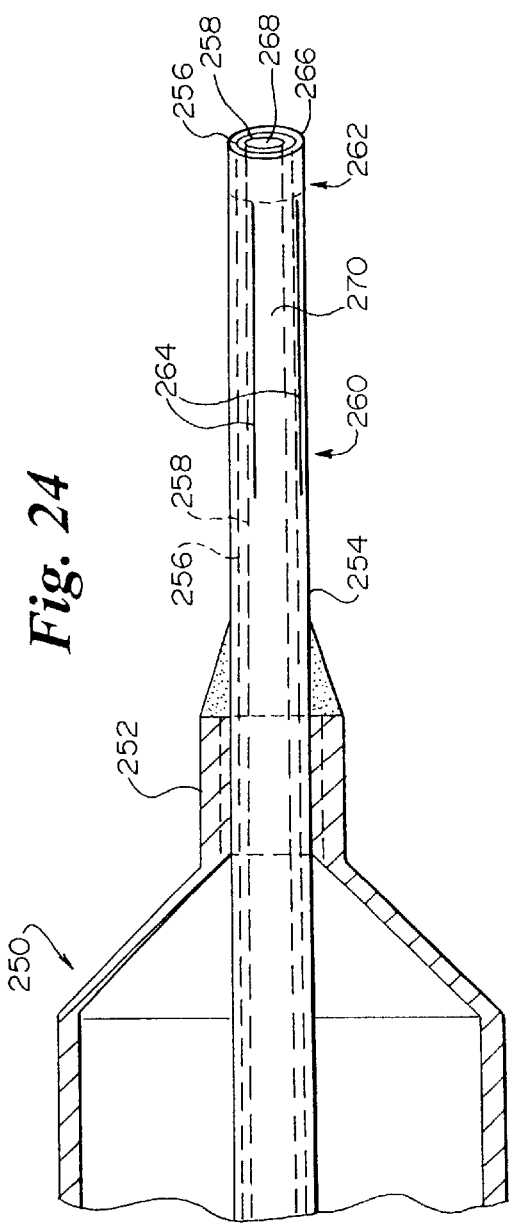
FIG. 24 is a fragmentary, longitudinal, cross-sectional view of an expandable catheter distal portion including a tube having distal slits and a tube slidably disposed within the tube and secured to the tube distal end.

Referring now to FIG. 24, a balloon assembly 250 is illustrated, including a balloon distal waist 252, an inner tube 254 having a distal region 260, a distal-most region 262, and a distal-most end 266. Inner tube 254 includes an inner tube wall 256 having a plurality of longitudinal slits 264 extending through distal region 260 and defining a plurality of flaps 270 therebetween. In a preferred embodiment, an innermost tube 258 is slidably disposed within inner tube 254. Inner tube 258 is preferably joined to inner tube 254 in distal-most region 262, for example, by adhesive application or bonding. In a preferred embodiment, inner tube 254 and innermost tube 258 are slidably disposed within much of distal region 260, but fixed relative to one another in distal-most region 262. In a preferred embodiment, distal region 260 is formed of a flexible polymeric material such as high density polyethylene. Innermost tube 258 preferably has a guide wire lumen 268 disposed therethrough. In an alternate embodiment, innermost tube 258 can be replaced by an innermost shaft or wire-like member not having a lumen within.

Figure 25:
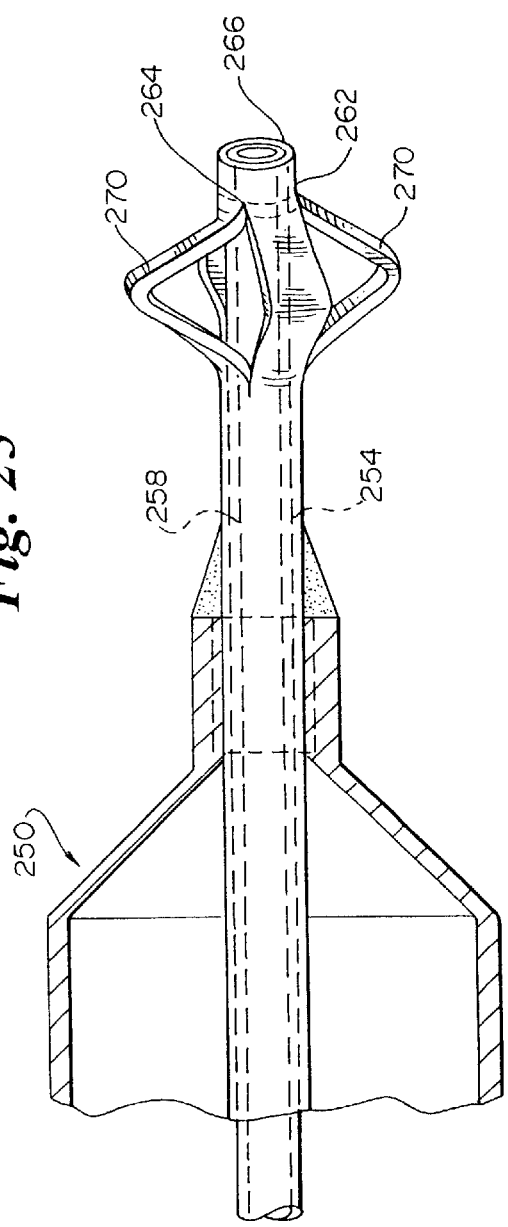
FIG. 25 is a fragmentary, longitudinal, cross-sectional view of the expandable catheter distal portion of FIG. 24, illustrated after the inner tube has been retracted, radially expanding the distal portion.

Referring now to FIG. 25, balloon assembly 250 of FIG. 24 is further illustrated in a second configuration having an increased cross-sectional profile or increased radial extent. Retracting innermost tube 258 relative to inner tube 254 causes flaps 270 to expand the radial extent of distal region 260. In use, balloon assembly 250 can be advanced to a location near a stent. Innermost tube 258 can be retracted within inner tube 254, thereby causing distal region 260 to expand as illustrated in FIG. 25. The increased radial extent and cross-sectional area of distal region 260 can act to deflect distal-most end 266 from stent walls and edges. Once distal-most end 266 has been sufficiently advanced, innermost tube 258 can be advanced relative to inner tube 254, thereby allowing flaps 270 to resume the smaller profile illustrated in FIG. 24.

Referring now to FIG. 26, a balloon catheter 300 is illustrated having a manifold 308, a shaft 309, and a balloon assembly 302. Shaft 309 includes a first inner tube or guide wire tube 304 including a first lumen 306 within terminating in a distal orifice 307. Manifold 308 includes a proximal tapered region 310 including a tapered lumen 311 therein. Manifold 308 includes a threaded region 314 connecting manifold 308 to an interconnect device 312. In one embodiment, first inner tube 304 has an inside diameter of about 0.035 inches. In another embodiment, first inner tube 304 has an inside diameter of about 0.018 inches.

Referring now to FIG. 27, an inner tube assembly 320 is illustrated having a second inner tube or guide wire tube 316 and a second guide wire lumen 318 disposed therein. Inner tube assembly 320 includes a proximal adapter 322 having a proximal lumen 324 disposed within and being in fluid communication with second guide wire lumen 318. Second inner tube 316 is sized to be received within first guide wire tube 304. Proximal adapter 322 is sized to be received within proximal tapered portion 310 of manifold 308. In one embodiment, second inner tube 316 has an inside diameter of about 0.014 inches. In one embodiment, second inner tube 316 has a length adapted to the length of first inner tube 304, such that when fully advanced into first inner tube 304, second inner tube 316 extends distally from first inner tube distal orifice 307.

In use, balloon catheter 300 may be advanced within the vasculature of a patient, bringing balloon assembly 302 to position near a target site. At that point, it may be desirable to further advance balloon assembly 302 to a more distant region of the vasculature and/or a more occluded region of the vasculature. This more distant and/or more occluded region may suggest the use of a smaller guide wire. Use of the smaller guide wire would aid in crossing a tight lesion or attaining position within a tortuous vascular region, but would be substantially smaller than the inside diameter of first guide wire lumen 306. At that point in time, the treating physician may wish to provide a second, smaller guide wire. This second smaller guide wire would receive improved support from a guide wire tube having a smaller inner diameter. The first guide wire can then be retracted from balloon catheter 300, and inner tube assembly 320 advanced distally into first guide wire lumen 306 of balloon catheter 300. With second inner tube 316 disposed within first inner tube 304, a smaller, second guide wire lumen 318 is provided. A second, smaller guide wire can be advanced through second guide wire lumen 318 until a location distal of balloon assembly 302 is reached. The second, smaller guide wire can be further advanced to the target site. The second, smaller guide wire can receive improved support against buckling by smaller, second guide wire lumen 318 provided within second inner tube 316.

In one embodiment, the second inner tube can extend distally from the first, surrounding, inner tube. The second inner tube can have the axial position adjusted such that the length of second tube extending distally from the first tube is varied. This can provide a distally protruding inner most tube, either with or without a guide wire disposed within. Distally advancing the inner most tube can provide a small profile which can be advantageous when crossing a constricted region. Proximally retracting the inner most tube can present a larger profile when desired.

In particular, it is recognized that the catheters of the present invention can include over-the-wire catheter designs, fixed wire catheter designs and single operator exchange catheter designs within the scope of the present disclosure.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A catheter tip assembly for crossing both vessel lumen obstructions or placed stents, said tip assembly comprising:
   an elongate tubular member having a proximal end, a distal end, and a guide wire receiving lumen and an inflation lumen extending therethrough;
   an inflatable balloon disposed proximate said distal end of said elongate tubular member, wherein a distal portion of said elongate tubular member extends distally beyond said inflatable balloon to form a catheter tip which defines a first tapered leading edge for crossing vessel lumen obstructions or placed stents, wherein said inflatable balloon has an interior in fluid communication with said inflation lumen; and
   a distal inflatable tip balloon disposed distal of said inflatable balloon, wherein said distal inflatable tip balloon has an interior in fluid communication with said inflatable balloon interior and said distal inflatable tip balloon is adapted and configured to shift between a first generally collapsed position and a second generally expanded position such that when in the second position a portion of an exterior surface of said distal inflatable tip balloon defines a second leading edge that aligns with said first tapered leading edge to aid in crossing a stent or vessel obstruction without said leading edge catching on a stent strut or vessel obstruction.

2. A catheter tip assembly as recited in claim 1, wherein said assembly includes a distal inflation lumen in fluid communication with said inflatable balloon interior and in fluid communication with said distal inflatable tip balloon interior.

3. A catheter tip assembly as recited in claim 2, wherein said assembly includes a valve operably disposed within said distal inflation lumen.

4. A catheter tip assembly as recited in claim 3, wherein said valve is a oneway valve, wherein said one-way valve allows a substantially greater rate of flow from said inflatable balloon to said distal inflatable tip balloon than from said distal inflatable tip balloon to said inflatable balloon.

5. A catheter tip assembly as recited in claim 2, further comprising means for slowly releasing fluid from said distal inflatable tip balloon.

6. A catheter tip assembly as recited in claim 4, further comprising an elongate valve control member coupled to said one-way valve.

7. A catheter tip assembly as recited in claim 6, wherein said elongate valve control member extends through said elongate tubular member and can be pulled proximally to open said valve, wherein said valve is biased to close.

8. A catheter tip assembly as recited in claim 6, wherein said elongate valve control member extends through said elongate tubular member and can be pulled proximally to open said valve, and can be pushed distally to close said valve.

9. A method for advancing a therapeutic catheter across a stent placed within a body vessel comprising the steps of:

providing a catheter including an elongate tubular member having a proximal end, a distal end, and a guide wire receiving lumen and an inflation lumen extending therethrough, an inflatable balloon disposed proximate said distal end of said elongate tubular member, said inflatable balloon having a maximum inflated radial extent, wherein a distal portion of said elongate tubular member extends distally beyond said inflatable to form a catheter tip which defines a leading edge for crossing a vessel obstruction or placed stent, wherein said inflatable balloon interior is in fluid communication with said inflation lumen, a distal inflatable member disposed distal of said balloon, wherein said distal inflatable member has an interior in fluid communication with said balloon interior, wherein said distal inflatable member has a maximum inflated radial extent that is less than said balloon maximum inflated radial extent, and a one-way valve in fluid communication with, and disposed between, said inflatable balloon interior and said distal inflatable member, wherein said one-way valve allows a substantially greater rate of flow from said balloon to said distal inflatable member than from said distal inflatable member to said balloon;

advancing said catheter into a body vessel;

providing inflation fluid to said inflatable balloon;

inflating said inflatable balloon and said distal inflatable member, such that said catheter distal region is radially expanded;

allowing said inflatable balloon to at least partially deflate; and advancing said catheter distal inflatable member through said stent.

\* \* \* \* \*

UNITED STATES PATENT AND TRADEMARK OFFICE
CERTIFICATE OF CORRECTION

PATENT NO. : 6,517,515 B1
DATED : February 11, 2003
INVENTOR(S) : Tracee E.J. Eidenschink It is certified that error appears in the above-identified patent and that said Letters Patent is hereby corrected as shown below:

Column 16,
Line 17, delete "comers" and insert therefor -- corners --.
Line 19, delete "comers" and insert therefor -- corners --.
Line 22, delete "comers" and insert therefor -- corners --.

Signed and Sealed this

Twenty-second Day of April, 2003

JAMES E. ROGAN
*Director of the United States Patent and Trademark Office*